United States Patent [19]

Gourlie et al.

[11] Patent Number: 5,472,693

[45] Date of Patent: Dec. 5, 1995

[54] FAMILY OF ANTI-CARCINOEMBRYONIC ANTIGEN CHIMERIC ANTIBODIES

[75] Inventors: Brian B. Gourlie; Mark W. Rixon; Peter S. Mezes, all of Midland, Mich.; Donald A. Kaplan, Cincinnati, Ohio; Jeffrey Schlom, Potomac, Md.

[73] Assignees: The Dow Chemical Company, Midland, Mich.; National Institutes of Health, Bethesda, Md.

[21] Appl. No.: 17,570

[22] Filed: Feb. 16, 1993

[51] Int. Cl.$^6$ .......................... C07K 16/28; A61K 39/395
[52] U.S. Cl. .................. 424/133.1; 435/69.1; 435/172.3; 435/240.27; 935/12; 935/15; 530/387.7; 424/138.1
[58] Field of Search ................................. 435/69.6, 172.3, 435/240.27; 530/387.7; 935/12, 15; 424/133.1, 138.1

[56] References Cited

U.S. PATENT DOCUMENTS

| | | |
|---|---|---|
| 4,642,334 | 2/1987 | Moore et al. |
| 4,656,134 | 4/1987 | Ringold. |
| 4,800,159 | 1/1989 | Mullis et al. |
| 5,075,431 | 12/1991 | Shively et al. |
| 5,081,235 | 1/1992 | Chively et al. ............... 536/23.52 |

FOREIGN PATENT DOCUMENTS

| | | |
|---|---|---|
| 0332424 | 9/1989 | European Pat. Off. |
| 9014424 | 11/1990 | WIPO |

OTHER PUBLICATIONS

Loh et al., Nature 276:785–790 (1978) "Rearrangement of Genetic Information may prod. Immuno. Diversity".
Schiff et al., J. of Exp. Med. 163:573–587 (Mar. 1986) "Genetic Basis for Exp. of the Idiotyp. Network: One Unique Ig. VH Germling Gene . . . ".
Waldmann, Science: 252:1657–1662 (1991) "Monoclonal Antibodies in Diagnosis & Therapy".
Dillman, Annals of Internal Medicine 111:592–603 (1989) "Monoclonal Antibodies for Treating Cancer".
Hird et al. Genes & Cancer, 1990, (Wiley & Sons, Ltd.) "Immunotherapy w/ Monoclonal Antibodies", pp. 183–184.
Manser et al. (1984), Proc. Natl. Acad. Sci., USA, 81:2470–2474.
Jones et al. (1986), Nature, 321:522–525.
Neuberger et al. (1984), Nature, 314:268–270.
Potter et al. (1984), Proc. Natl. Acad. Sci. USA, 81:7161–7165.
Oi, et al. (1983), Proc. Natl. Acad. Sci. USA 80:825–829.
Cabilly et al. (1984), Proc. Natl Aca Sci, USA, 81:3273–3277.
Kenten et al. (1984), Proc. Natl. Aca. Sci., USA, 81:2955–2959.
Lui et al. (1984), Proc. Natl. Acad. Sci., USA, 81:5369–5373.
Neuberger et al. (1984), Nature, 312:604–608.
Shaw et al. (1987), The Journal of Immunology, 138(2):4534–4538.
Boulianne et al. (1984), Nature, 312:643–64.
Sun et al. (1986), Hybridoma, 5(Suppl. 1):S17–S20.
Lui et al. (1987), Proc. Natl. Acad. Sci., USA, 84:3439–3443.
Brown et al. (1987), Cancer Research, 47:3577–3583.
Morrison et al. (1984), Proc. Natl. Acad. Sci., USA, 81:6851–6855.
Rice, et al., (1982), Proc. Natl. Acad. Sci., USA, 79:7862–7865.

Primary Examiner—Margaret Parr
Assistant Examiner—T. Michael Nisbet
Attorney, Agent, or Firm—D. Culmer; K. L. Kimble

[57] ABSTRACT

The present invention discloses novel chimeric monoclonal antibodies directed against human carcinoembryonic antigen, having antigen-specific variable regions. DNA constructs for the light and heavy chain variable regions comprising the novel antibodies of the invention are also disclosed. Eukaryotic host cells capable of expression of the chimeric antibodies and comprising the novel chimeric antibody-encoding DNA constructs are also described.

10 Claims, 5 Drawing Sheets

5,472,693

SEQUENCE LISTING ( 1 ) GENERAL INFORMATION:

(  i i i ) NUMBER OF SEQUENCES: 24

( 2 ) INFORMATION FOR SEQ ID NO:1:

( i ) SEQUENCE CHARACTERISTICS:
       ( A ) LENGTH: 331 base pairs
       ( B ) TYPE: nucleic acid
       ( C ) STRANDEDNESS: double
       ( D ) TOPOLOGY: linear ( i i ) MOLECULE TYPE: cDNA ( v i ) ORIGINAL SOURCE:
       ( A ) ORGANISM: Mus muscaris ( i x ) FEATURE:
       ( A ) NAME/KEY: CDS
       ( B ) LOCATION: 1..331

( x i ) SEQUENCE DESCRIPTION: SEQ ID NO:1:

| GAC | ATT | GTG | CTG | ACA | CAG | TCT | CCT | GCT | TCC | TTA | ACT | GTA | TCT | CTG | GGG | 48 |
| Asp | Ile | Val | Leu | Thr | Gln | Ser | Pro | Ala | Ser | Leu | Thr | Val | Ser | Leu | Gly | |
| 1 | | | | 5 | | | | | 10 | | | | | 15 | | |

| CTG | AGG | GCC | ACC | ATC | TCA | TGC | AGG | GCC | AGC | AAA | AGT | GTC | AGT | GCA | TCT | 96 |
| Leu | Arg | Ala | Thr | Ile | Ser | Cys | Arg | Ala | Ser | Lys | Ser | Val | Ser | Ala | Ser | |
| | | | 20 | | | | | 25 | | | | | 30 | | | |

| GGC | TAT | AGT | TAT | ATG | CAC | TGG | TAC | CAA | CAG | AGA | CCA | GGA | CAG | CCA | CCC | 144 |
| Gly | Tyr | Ser | Tyr | Met | His | Trp | Tyr | Gln | Gln | Arg | Pro | Gly | Gln | Pro | Pro | |
| | | 35 | | | | | 40 | | | | | 45 | | | | |

| AAA | CTC | CTC | ATC | TAT | CTT | GCA | TCC | AAC | CTA | CAA | TCT | GGG | GTC | CCT | GCC | 192 |
| Lys | Leu | Leu | Ile | Tyr | Leu | Ala | Ser | Asn | Leu | Gln | Ser | Gly | Val | Pro | Ala | |
| 50 | | | | | 55 | | | | | 60 | | | | | | |

| AGG | TTC | AGT | GGC | AGT | GGG | TCT | GGG | ACA | GAC | TTC | ACC | CTC | AAC | ATC | CAT | 240 |
| Arg | Phe | Ser | Gly | Ser | Gly | Ser | Gly | Thr | Asp | Phe | Thr | Leu | Asn | Ile | His | |
| 65 | | | | | 70 | | | | | 75 | | | | | 80 | |

| CCT | GTG | GAG | GAG | GAG | GAT | GCT | GCA | ACC | TAT | TAC | TGT | CAG | CAC | AGT | AGG | 288 |
| Pro | Val | Glu | Glu | Glu | Asp | Ala | Ala | Thr | Tyr | Tyr | Cys | Gln | His | Ser | Arg | |
| | | | | 85 | | | | | 90 | | | | | 95 | | |

| GAG | CTT | CCG | ACG | TTC | GGT | GGA | GGC | ACC | AAG | CTG | GAA | ATC | AAA | C | | 331 |
| Glu | Leu | Pro | Thr | Phe | Gly | Gly | Gly | Thr | Lys | Leu | Glu | Ile | Lys | | | |
| | | | 100 | | | | | 105 | | | | | 110 | | | |

( 2 ) INFORMATION FOR SEQ ID NO:2:

( i ) SEQUENCE CHARACTERISTICS:
       ( A ) LENGTH: 110 amino acids
       ( B ) TYPE: amino acid
       ( D ) TOPOLOGY: linear ( i i ) MOLECULE TYPE: protein ( x i ) SEQUENCE DESCRIPTION: SEQ ID NO:2:

| Asp | Ile | Val | Leu | Thr | Gln | Ser | Pro | Ala | Ser | Leu | Thr | Val | Ser | Leu | Gly |
| 1 | | | | 5 | | | | | 10 | | | | | 15 | |

| Leu | Arg | Ala | Thr | Ile | Ser | Cys | Arg | Ala | Ser | Lys | Ser | Val | Ser | Ala | Ser |
| | | | 20 | | | | | 25 | | | | | 30 | | |

| Gly | Tyr | Ser | Tyr | Met | His | Trp | Tyr | Gln | Gln | Arg | Pro | Gly | Gln | Pro | Pro |
| | | 35 | | | | | 40 | | | | | 45 | | | |

| Lys | Leu | Leu | Ile | Tyr | Leu | Ala | Ser | Asn | Leu | Gln | Ser | Gly | Val | Pro | Ala |
| 50 | | | | | 55 | | | | | 60 | | | | | |

| Arg | Phe | Ser | Gly | Ser | Gly | Ser | Gly | Thr | Asp | Phe | Thr | Leu | Asn | Ile | His |
| 65 | | | | | 70 | | | | | 75 | | | | | 80 |

| Pro | Val | Glu | Glu | Glu | Asp | Ala | Ala | Thr | Tyr | Tyr | Cys | Gln | His | Ser | Arg |

|  |  |  | 85 |  |  |  |  | 90 |  |  |  |  | 95 |  |  |
|--|--|--|--|--|--|--|--|--|--|--|--|--|--|--|--|
| Glu | Leu | Pro | Thr | Phe | Gly | Gly | Gly | Thr | Lys | Leu | Glu | Ile | Lys |  |  |
|  |  |  | 100 |  |  |  |  | 105 |  |  |  |  | 110 |  |  |

(2) INFORMATION FOR SEQ ID NO:3:

(i) SEQUENCE CHARACTERISTICS:
    (A) LENGTH: 373 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Mus muscaris (ix) FEATURE:
    (A) NAME/KEY: CDS
    (B) LOCATION: 1..373

(xi) SEQUENCE DESCRIPTION: SEQ ID NO:3:

| GAG | GTT | CAG | CTG | CAG | CAG | TCT | GGG | GCA | GAG | CTT | GTG | AGG | TCA | GGG | GCC | 48 |
|--|--|--|--|--|--|--|--|--|--|--|--|--|--|--|--|--|
| Glu | Val | Gln | Leu | Gln | Gln | Ser | Gly | Ala | Glu | Leu | Val | Arg | Ser | Gly | Ala |  |
| 1 |  |  |  | 5 |  |  |  |  | 10 |  |  |  |  | 15 |  |  |

| TCA | GTC | AAG | ATG | TCC | TGC | ACA | GCT | TCT | GGC | TTC | AAC | ATT | AAA | GAC | TAC | 96 |
|--|--|--|--|--|--|--|--|--|--|--|--|--|--|--|--|--|
| Ser | Val | Lys | Met | Ser | Cys | Thr | Ala | Ser | Gly | Phe | Asn | Ile | Lys | Asp | Tyr |  |
|  |  |  | 20 |  |  |  |  | 25 |  |  |  |  | 30 |  |  |  |

| TAT | ATG | CAC | TGG | GTG | AAG | CAG | AGG | CCT | GAA | CAG | GGC | CTG | GAG | TGG | ATT | 144 |
|--|--|--|--|--|--|--|--|--|--|--|--|--|--|--|--|--|
| Tyr | Met | His | Trp | Val | Lys | Gln | Arg | Pro | Glu | Gln | Gly | Leu | Glu | Trp | Ile |  |
|  |  | 35 |  |  |  |  | 40 |  |  |  |  | 45 |  |  |  |  |

| GGA | TGG | ATT | GAT | CCT | GAG | AAT | GGT | GAT | ACT | GAA | TAT | GCC | CCG | AAG | TTC | 192 |
|--|--|--|--|--|--|--|--|--|--|--|--|--|--|--|--|--|
| Gly | Trp | Ile | Asp | Pro | Glu | Asn | Gly | Asp | Thr | Glu | Tyr | Ala | Pro | Lys | Phe |  |
|  | 50 |  |  |  |  | 55 |  |  |  |  | 60 |  |  |  |  |  |

| CAG | GGC | AAG | GCC | ACT | ATG | ACT | ACA | GAC | ACA | TCC | TCC | AAC | ACA | GCC | TAC | 240 |
|--|--|--|--|--|--|--|--|--|--|--|--|--|--|--|--|--|
| Gln | Gly | Lys | Ala | Thr | Met | Thr | Thr | Asp | Thr | Ser | Ser | Asn | Thr | Ala | Tyr |  |
| 65 |  |  |  |  | 70 |  |  |  |  | 75 |  |  |  |  | 80 |  |

| CTG | CAG | CTC | AGC | AGC | CTG | ACA | TCT | GAG | GAC | ACT | GCC | GTC | TAT | TAC | TGT | 288 |
|--|--|--|--|--|--|--|--|--|--|--|--|--|--|--|--|--|
| Leu | Gln | Leu | Ser | Ser | Leu | Thr | Ser | Glu | Asp | Thr | Ala | Val | Tyr | Tyr | Cys |  |
|  |  |  |  | 85 |  |  |  |  | 90 |  |  |  |  | 95 |  |  |

| AAT | ACA | CGG | GGT | CTA | TCT | ACT | ATG | ATT | ACG | ACG | CGT | TGG | TTC | TTC | GAT | 336 |
|--|--|--|--|--|--|--|--|--|--|--|--|--|--|--|--|--|
| Asn | Thr | Arg | Gly | Leu | Ser | Thr | Met | Ile | Thr | Thr | Arg | Trp | Phe | Phe | Asp |  |
|  |  |  | 100 |  |  |  |  | 105 |  |  |  |  | 110 |  |  |  |

| GTC | TGG | GGC | GCA | GGG | ACC | ACG | GTC | GCC | GTC | TCC | TCT | G |  |  |  | 373 |
|--|--|--|--|--|--|--|--|--|--|--|--|--|--|--|--|--|
| Val | Trp | Gly | Ala | Gly | Thr | Thr | Val | Ala | Val | Ser | Ser |  |  |  |  |  |
|  |  | 115 |  |  |  |  | 120 |  |  |  |  |  |  |  |  |  |

(2) INFORMATION FOR SEQ ID NO:4:

(i) SEQUENCE CHARACTERISTICS:
    (A) LENGTH: 124 amino acids
    (B) TYPE: amino acid
    (D) TOPOLOGY: linear (ii) MOLECULE TYPE: protein (xi) SEQUENCE DESCRIPTION: SEQ ID NO:4:

| Glu | Val | Gln | Leu | Gln | Gln | Ser | Gly | Ala | Glu | Leu | Val | Arg | Ser | Gly | Ala |
|--|--|--|--|--|--|--|--|--|--|--|--|--|--|--|--|
| 1 |  |  |  | 5 |  |  |  |  | 10 |  |  |  |  | 15 |  |

| Ser | Val | Lys | Met | Ser | Cys | Thr | Ala | Ser | Gly | Phe | Asn | Ile | Lys | Asp | Tyr |
|--|--|--|--|--|--|--|--|--|--|--|--|--|--|--|--|
|  |  |  | 20 |  |  |  |  | 25 |  |  |  |  | 30 |  |  |

| Tyr | Met | His | Trp | Val | Lys | Gln | Arg | Pro | Glu | Gln | Gly | Leu | Glu | Trp | Ile |
|--|--|--|--|--|--|--|--|--|--|--|--|--|--|--|--|
|  |  | 35 |  |  |  |  | 40 |  |  |  |  | 45 |  |  |  |

| Gly | Trp | Ile | Asp | Pro | Glu | Asn | Gly | Asp | Thr | Glu | Tyr | Ala | Pro | Lys | Phe |
|--|--|--|--|--|--|--|--|--|--|--|--|--|--|--|--|

|  |  |  |  |  | 50 |  |  |  |  | 55 |  |  |  |  | 60 |  |  |
|---|---|---|---|---|----|---|---|---|---|----|---|---|---|---|----|---|---|

Gln Gly Lys Ala Thr Met Thr Thr Asp Thr Ser Ser Asn Thr Ala Tyr
65                      70                      75                      80

Leu Gln Leu Ser Ser Leu Thr Ser Glu Asp Thr Ala Val Tyr Tyr Cys
                85                      90                      95

Asn Thr Arg Gly Leu Ser Thr Met Ile Thr Thr Arg Trp Phe Phe Asp
            100                     105                     110

Val Trp Gly Ala Gly Thr Thr Val Ala Val Ser Ser
        115                     120

( 2 ) INFORMATION FOR SEQ ID NO:5:

( i ) SEQUENCE CHARACTERISTICS:
        ( A ) LENGTH: 373 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..373

( x i ) SEQUENCE DESCRIPTION: SEQ ID NO:5:

GAG GTT CAG CTG CAG CAG TCT GGG GCA GAG CTT GTG AGG TCA GGG GCC       48
Glu Val Gln Leu Gln Gln Ser Gly Ala Glu Leu Val Arg Ser Gly Ala
1               5                   10                  15

TCA GTC AAG ATG TCC TGC ACA GCT TCT GGC TTC AAC ATT AAA GAC TAC       96
Ser Val Lys Met Ser Cys Thr Ala Ser Gly Phe Asn Ile Lys Asp Tyr
            20                  25                  30

TAT ATG CAC TGG GTG AAG CAG AGG CCT GAA CAG GGC CTG GAG TGG ATT      144
Tyr Met His Trp Val Lys Gln Arg Pro Glu Gln Gly Leu Glu Trp Ile
        35                  40                  45

GGA TGG ATT GAT CCT GAG AAT GGT GAT ACT GAA TAT GCC CCG AAG TTC      192
Gly Trp Ile Asp Pro Glu Asn Gly Asp Thr Glu Tyr Ala Pro Lys Phe
    50                  55                  60

CAG GGC AAG GCC ACT ATG ACT ACA GAC ACA TCC TCC AAC ACA GCC TAC      240
Gln Gly Lys Ala Thr Met Thr Thr Asp Thr Ser Ser Asn Thr Ala Tyr
65                  70                  75                  80

CTG CAG CTC AGC AGC CTG ACA TCT GAG GAC ACT GCC GTC TAT TAC TGT      288
Leu Gln Leu Ser Ser Leu Thr Ser Glu Asp Thr Ala Val Tyr Tyr Cys
                85                  90                  95

AAT ACA CGG GGT CTA TCT ACT ATG ATT ACG ACG CGT TGG TTC TTC GAT      336
Asn Thr Arg Gly Leu Ser Thr Met Ile Thr Thr Arg Trp Phe Phe Asp
            100                 105                 110

GTC TGG GGC GCA GGG ACC ACG GTC ACC GTC TCC TCA G                    373
Val Trp Gly Ala Gly Thr Thr Val Thr Val Ser Ser
        115                 120

( 2 ) INFORMATION FOR SEQ ID NO:6:

( i ) SEQUENCE CHARACTERISTICS:
        ( A ) LENGTH: 124 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

Glu Val Gln Leu Gln Gln Ser Gly Ala Glu Leu Val Arg Ser Gly Ala
1               5                   10                  15

Ser Val Lys Met Ser Cys Thr Ala Ser Gly Phe Asn Ile Lys Asp Tyr

|          |          |          |          |          | 20       |          |          |          | 25       |          |          |          | 30       |          |          |
|----------|----------|----------|----------|----------|----------|----------|----------|----------|----------|----------|----------|----------|----------|----------|----------|
| Tyr      | Met      | His      | Trp      | Val      | Lys      | Gln      | Arg      | Pro      | Glu      | Gln      | Gly      | Leu      | Glu      | Trp      | Ile      |
|          |          | 35       |          |          |          |          | 40       |          |          |          |          | 45       |          |          |          |
| Gly      | Trp      | Ile      | Asp      | Pro      | Glu      | Asn      | Gly      | Asp      | Thr      | Glu      | Tyr      | Ala      | Pro      | Lys      | Phe      |
|          | 50       |          |          |          |          | 55       |          |          |          |          | 60       |          |          |          |          |
| Gln      | Gly      | Lys      | Ala      | Thr      | Met      | Thr      | Thr      | Asp      | Thr      | Ser      | Ser      | Asn      | Thr      | Ala      | Tyr      |
| 65       |          |          |          |          | 70       |          |          |          |          | 75       |          |          |          |          | 80       |
| Leu      | Gln      | Leu      | Ser      | Ser      | Leu      | Thr      | Ser      | Glu      | Asp      | Thr      | Ala      | Val      | Tyr      | Tyr      | Cys      |
|          |          |          |          | 85       |          |          |          |          | 90       |          |          |          |          | 95       |          |
| Asn      | Thr      | Arg      | Gly      | Leu      | Ser      | Thr      | Met      | Ile      | Thr      | Thr      | Arg      | Trp      | Phe      | Phe      | Asp      |
|          |          |          | 100      |          |          |          |          | 105      |          |          |          |          | 110      |          |          |
| Val      | Trp      | Gly      | Ala      | Gly      | Thr      | Thr      | Val      | Thr      | Val      | Ser      | Ser      |          |          |          |          |
|          |          | 115      |          |          |          |          | 120      |          |          |          |          |          |          |          |          |

( 2 ) INFORMATION FOR SEQ ID NO:7:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GAGGAGACGG TGACCGTGGT CCC                                      23

( 2 ) INFORMATION FOR SEQ ID NO:8:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CACTATGACT ACAGACACAT CCTC                                    24

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GAGGATGTGT CTGTAGTCAT AGTG                                    24

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CTCTGTGACA GTGGCAATCA C                                          21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single ( D ) TOPOLOGY: linear ( x i ) SEQUENCE DESCRIPTION: SEQ ID NO:11:

GTGATTGCCA CTGTCACAGA G     21

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GGAAGATGGA TACAGTTGGT GC     22

( 2 ) INFORMATION FOR SEQ ID NO:13:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CGTTTGATTT CCAGCTTGGT GCC     23

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

CAGACCCACT GCCACTGAAC C     21

( 2 ) INFORMATION FOR SEQ ID NO:15:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 4..9
        ( D ) OTHER INFORMATION: /label=BamHI_site ( x i ) SEQUENCE DESCRIPTION: SEQ ID NO:15:

CTCGGATCCT CATTGTCCAT TACTGACTAC AGGTGCCTAC GGTGACATTG TGCTGACACA     60

G     61

( 2 ) INFORMATION FOR SEQ ID NO:16:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i x ) FEATURE:
        ( A ) NAME/KEY: misc_feature
        ( B ) LOCATION: 5..10
        ( D ) OTHER INFORMATION: /label=HindIII_site ( x i ) SEQUENCE DESCRIPTION: SEQ ID NO:16:

CATTAAGCTT AGAAAAGTGT ACTTACGTTT GATTTCCAGC TTGGTGCC 48

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

AGAGGATATT GAAATAATTA AATAGCAC 28

( 2 ) INFORMATION FOR SEQ ID NO:18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

GGCCCTTTCG TCTTCAAGAA TTC 23

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

TATCTTATCA TGTCTGGATC C 21

( 2 ) INFORMATION FOR SEQ ID NO:20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:20:

GGTAAATGAG TGCGACGG 18

( 2 ) INFORMATION FOR SEQ ID NO:21:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:21:

CCGTCGCACT CATTTACCAA CTCTCTTGTC CACCTT 36

( 2 ) INFORMATION FOR SEQ ID NO:22:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:22:

CCGTCGCACT CATTTACCTG GGCACGGTGG GCATGT     36

(2) INFORMATION FOR SEQ ID NO:23:

(i) SEQUENCE CHARACTERISTICS:
(A) LENGTH: 34 base pairs
(B) TYPE: nucleic acid
(C) STRANDEDNESS: single
(D) TOPOLOGY: linear (xi) SEQUENCE DESCRIPTION: SEQ ID NO:23:

GATGCGGCCG CTCTTACCTG AGGAGACGGT GACC     34

(2) INFORMATION FOR SEQ ID NO:24:

(i) SEQUENCE CHARACTERISTICS:
(A) LENGTH: 26 base pairs
(B) TYPE: nucleic acid
(C) STRANDEDNESS: single
(D) TOPOLOGY: linear (xi) SEQUENCE DESCRIPTION: SEQ ID NO:24:

CGTGTCGACA GGCATCAATT CAGAGG     26

FAMILY OF ANTI-CARCINOEMBRYONIC ANTIGEN CHIMERIC ANTIBODIES

FIELD OF THE INVENTION

The present invention relates to novel chimeric antibodies directed against human carcinoembryonic antigen, and DNA constructs coding for such antibodies.

BACKGROUND OF THE INVENTION

Carcinoembryonic antigen (CEA) is the best characterized human tumor-associated antigen and the most widely used tumor marker for the in vitro diagnosis of human colon cancers. CEA is one of a family of closely related gene products including normal fecal antigen, non-specific cross-reacting antigen, meconium antigen, and biliary glycoprotein. See, for example, Muraro et al. *Cancer Research*, 45:5769–5780 (1985); and Rodgers *Biochim. Biophys. Aca*, 695:227–249 (1983).

The development of antigen-specific monoclonal antibodies (MAbs) for in vitro and in vivo diagnosis and therapy has resulted in the production of a MAb which has an affinity constant in the range of $2.6 \times 10^{10}$ $M^{-1}$ for CEA (U.S. Pat. No. 5,075,432; T84.66 ATCC Accession No. BH 8747) and little or no cross reactivity to other members of the CEA gene family.

Most available MAbs, however, are derived from murine hybridomas. The in vitro application of murine antibodies in immunoassays presents potential problems associated with false positive results which are attributable to the reaction of serum components with murine immunoglobulins. More importantly however, the in vivo application of murine antibodies in human medicine is often limited due to their inherent immunogenicity. The administration of murine antibodies will, in many patients, induce an immune response which results in a gradual decline in the efficacy of the antibodies during multiple dose regimens. The decrease in efficacy is attributable, at least in part, to the rapid clearance from circulation or alteration of pharmacokinetic properties of murine antibodies by the patient's immune response. The immunogenicity associated with murine monoclonal antibodies, therefore, precludes multiple dose administrations over an extended period of time, or even a single administration if there has been prior exposure, and substantially impacts their potential clinical value.

Chimeric antibodies, in which the binding or variable regions of antibodies derived from one species are combined with the constant regions of antibodies derived from a different species, have been constructed by recombinant DNA methodology. See, for example, Sahagen et al., *J. Immunol.*, 137:1066–1074 (1986); Sun et al., *Proc. Natl. Acad. Sci. USA*, 82:214–218 (1987); Nishimura et al., *Cancer Res.*, 47:999–1005 (1987); and Lie et al. *Proc. Natl. Acad. Sci. USA*, 84:3439–3443 (1987) which describe chimeric antibodies to tumor-associated antigens. Typically, the variable region of a murine antibody is joined with the constant region of a human antibody. It is expected that, as such, chimeric antibodies are largely human in composition, and will be substantially less immunogenic than murine antibodies. Accordingly, chimeric antibodies are highly desirable for in vivo application.

While the general concept of chimeric antibodies has been described, it is known that the function of antibody molecules is dependent on its three dimensional structure, which in turn is dependent on its primary amino acid structure. Thus, changing the amino acid sequence of an antibody may adversely affect its activity, see for example, Horgan et al., *J. Immunology*, 149:127–135 (1992). Moreover, a change in the DNA sequence coding for an antibody may affect the ability of the cell containing the DNA sequence to express, secrete or assemble the antibody.

Although chimeric antibodies against tumors have been described, there exists a need for the development of novel chimeric antibodies having specificity for antigens of human CEA.

SUMMARY OF THE INVENTION

The present invention provides expression vectors containing DNA sequences which encode chimeric COL-1 (ChCOL-1) or chimeric COL-1R' (ChCOL-1R') antibodies and portions thereof which are directed against CEA, using murine variable regions and human constant region genes. In particular, the present invention is a chimeric murine-human COL-1 or COL-1R' antibody having a light chain variable region substantially the same as that encoded by the nucleotide sequence of SEQ ID NO:1. In another aspect, the present invention is a chimeric murine-human COL-1 antibody having a heavy chain variable region substantially the same as that encoded by the DNA sequence of SEQ ID NO:3 or a chimeric murine-human COL-1R' antibody having a heavy chain variable region substantially the same as that encoded by the DNA sequence of SEQ ID NO:5.

The present invention also provides cells transformed with expression vectors containing a DNA sequence which encodes for chimeric COL-1 or chimeric COL-1 R' antibodies.

In another aspect, the present invention provides a ChCOL-1 or ChCOL-1R' monoclonal antibody comprising a light chain variable region having the amino acid sequence substantially the same as that of SEQ ID NO:2. The present invention further provides a ChCOL-1 or ChCOL-1R' monoclonal antibody comprising a heavy chain variable region having the amino acid sequence substantially the same as that of SEQ ID NO:4 or SEQ ID NO:6. In still another aspect, the present invention provides a chimeric monoclonal antibody comprising a light chain variable region having an amino acid sequence substantially the same as that of SEQ ID NO:2 and a heavy chain variable region having an amino acid sequence substantially the same as that of SEQ IN NO:4 or substantially the same as that of SEQ ID NO:6.

In addition, the present invention provides novel chimeric antibodies for use in in vitro and diagnostic assays and in vitro therapy.

DETAILED DESCRIPTION OF THE INVENTION

Figure 1:
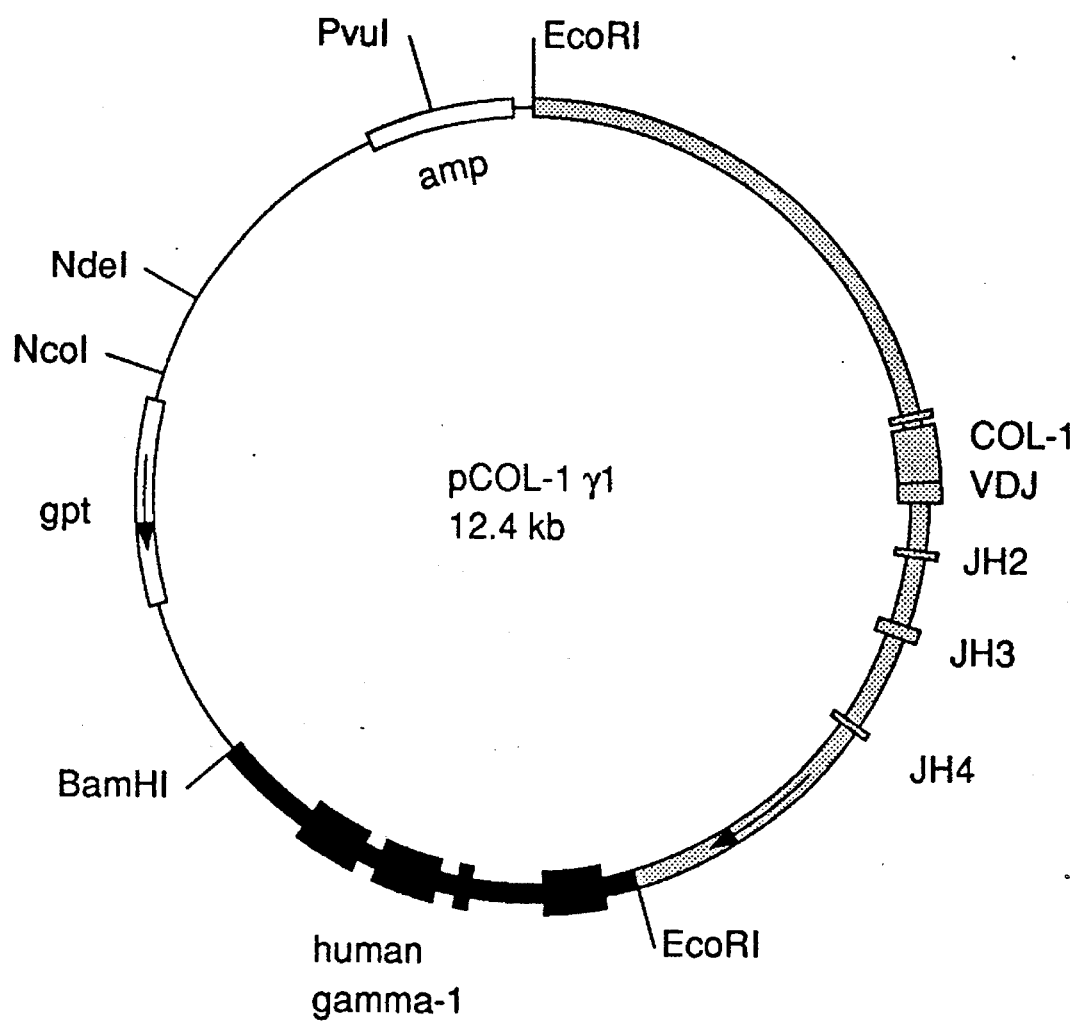
FIG. 1 illustrates the plasmid map of pCOL-1 γ1. The murine COL-1 heavy chain variable region is indicated by the stippled bar and the human γ1 constant region is indicated by the black bar.

The entire teaching of all references cited herein are hereby incorporated by reference. The procedures for molecular cloning are as those described in Sambrook et al., *Molecular Cloning*, Cold Spring Harbor Press, New York, 2nd Ed. (1989) and Ausubel et al., *Current Protocols in Molecular Biology*, John Wiley and Sons, New York (1992).

Nucleic acids, amino acids, peptides, protective groups, active groups and such, when abbreviated, are abbreviated according to the IUPAC IUB (Commission on Biological Nomenclature) or the practice in the fields concerned.

As used herein, the term "variable region" refers to the region, or domain, of the light ($V_L$) and heavy ($V_H$) chain antibody molecules which contain the determinants for binding recognition specificity to the antigen and overall affinity of a MAb. The variable domains of each pair of light and heavy chains form the antigen binding site. The domains of the light and heavy chains have the same general structure and each domain has four framework (FR) regions, whose sequences are relatively conserved, connected by three complementarity determining regions (CDRs). The FR regions maintain structural integrity of the variable domain. The CDRs are the polypeptide segments within the variable domain that mediate binding of the antigen.

The term "constant region", as used herein, refers to the domain of the light ($C_L$) and heavy ($C_H$) chain antibody molecules which provide structural stability and other biological functions such as antibody chain association, secretion, transplacental mobility, and complement binding, but is not involved with binding CEA. The amino acid sequence and corresponding exon sequences in the genes of the constant region will be dependent upon the species from which it is derived; however, variations in the amino acid sequence leading to allotypes will be relatively limited for particular constant regions within a species.

The variable region of each chain is joined to the constant region by a linking polypeptide sequence. The linkage sequence is coded by a "J" sequence in the light chain gene, and a combination of a "D" sequence and a "J" sequence in the heavy chain gene.

"Chimeric antibody" for purposes of this invention refers to an antibody having in the heavy and light chain a variable region amino acid sequence encoded by a nucleotide sequence derived from a murine immunoglobulin gene and a constant region amino acid sequence encoded by a nucleotide sequence derived from a human immunoglobulin gene.

As used herein, the term "transformation" refers to the change in the genome of a host cell by introduction of DNA into the recipient host cell. "Host cells" refer to cells which can be transformed with vectors constructed using recombinant DNA techniques, and for the vectors to persist within the cell for expression of a recombinant protein product.

As used herein, the terms "antibody" or "immunoglobulin" include segments of proteolytically-cleaved or recombinantly-prepared portions of an antibody molecule that are capable of selectively reacting with a particular antigen or antigen family. Nonlimiting examples of such proteolytic and/or recombinant fragments include Fab, F(ab')$_2$, Fab', Fv, fragments, and single chain antibodies (scFv) containing a $V_L$ and $V_H$ domain joined by a peptide linker. The scFv's may be covalently or non-covalently linked to form antibodies having two or more binding sites.

The DNA coding sequences of the present invention have a first DNA sequence encoding the light or heavy chain variable domains having a specificity for CEA and a second DNA sequence encoding the light or heavy chain constant domains of chimeric antibodies.

In accordance with the present invention, DNA constructs for the light chains of chimeric antibodies directed against CEA comprise a first DNA sequence encoding a light chain variable region which is substantially the same as that of SEQ ID NO:1.

Also, in accordance with the present invention, DNA constructs for heavy chains of chimeric antibodies directed against CEA comprise a first DNA sequence encoding for a heavy chain variable region which is substantially the same as that of SEQ ID NO:3 or SEQ ID NO:5.

The amino acid sequences of the chimeric polypeptides comprising the novel chimeric antibodies of the present invention can be determined from the DNA sequences disclosed herein. Accordingly, the COL-1 and COL-1R' chimeric antibodies of the present invention directed against CEA comprise a light chain variable region having an amino acid sequence substantially the same as that of SEQ ID NO:2. Additionally, the novel chimeric antibodies of the present invention comprise a heavy chain variable region having an amino acid sequence substantially the same as that of SEQ ID NO:4 or SEQ ID NO:6.

"Substantially the same" means minor modifications to the nucleotide sequences encoding or amino acid sequences of the chimeric polypeptides disclosed herein which would result in variable regions that are substantially equivalent in the binding of CEA. These modifications are contemplated by the present invention provided the requisite specificity for CEA is retained.

The CDRs from the variable regions of the COL-1 and COL-1R' antibodies may be grafted onto human FR regions, see, for example, EPO Publication No. 0239400. These new antibodies are called humanized antibodies and the process by which the murine antibody is converted into a human antibody by combining the CDRs with a human FR is called humanization. Humanized antibodies are important because they bind to the same antigen as the original antibodies but, again, like the chimeric antibodies, are less immunogenic when injected into humans. The CDRs of the COL-1 light chain variable domain are represented in SEQ ID NO:2 by amino acid positions 24 to 38 for CDR1, 54 to 60 for CDR2 and 93 to 100 for CDR3. The CDRs of the COL-1 and COL-1R' heavy chain variable domains are represented in SEQ ID NO:4 and SEQ ID NO:6 by amino acid positions 31 to 35 for CDR1, 50 to 66 for CDR2 and 99 to 113 for CDR3.

Preferably, the first DNA coding sequences for the light and heavy chain variable regions comprise a DNA sequence coding for a leader peptide for expression and secretion of these polypeptides by eukaryotic host cells. The DNA sequences for a leader peptide include a translational start signal, i.e., a sequence within the transcribed mRNA sequence that initiates translation of functional polypeptides. Those skilled in the art will recognize that, as the leader peptide is not present in the mature protein and does not function in the binding of CEA, various DNA sequences encoding for leader peptides may be suitably utilized in the present invention. Prior to secretion of the mature polypeptides, the nascent light and heavy chain polypeptides are cleaved at the signal peptide cleavage site, which removes the leader peptides or signal sequences from each of the chains.

It will be appreciated by those skilled in the art that the first DNA coding sequences comprising the DNA constructs of the invention may be modified by a number of methods known in the art, for example, by site-directed mutagenesis to provide DNA constructs which are substantially equivalent. These modified DNA coding sequences are included in the invention provided they are capable of being translated into substantially the same chimeric polypeptides as described herein. The use of site-directed mutagenesis may, in certain cases, modify the affinity of the resulting chimeric polypeptides for CEA.

Preferably, the first DNA coding sequences of the DNA constructs of the present invention are derived from the genomic DNA of a murine hybridoma expressing monoclonal antibody directed against CEA, designated COL-1, see, for example, Muraro et al., supra.

Genomic DNA for use in the invention can be obtained and cloned by conventional techniques and in a variety of ways. Such techniques are described in *Basic Methods in Molecular Biology*, edited by Davis et al., Elsevier, New York (1986); Sambrook et al., Molecular Cloning, Cold Spring Harbor Press, New York, 2nd Ed. (1989) and Ausubel et al., *Current Protocols in Molecular Biology*, John Wiley and Sons, New York (1992). For example, hybridoma cellular DNA may be isolated by standard procedures, the genomic DNA digested into fragments by restriction endonucleases, and the resulting fragments cloned into suitable recombinant DNA cloning vectors and screened with radiolabeled or enzymatically labeled probes for the presence of the DNA sequences disclosed herein.

The first DNA sequences of the DNA constructs of the invention, encoding for polypeptides which are light and heavy chain variable regions of chimeric antibodies, can also be obtained from cDNA derived from hybridom mRNA. Procedures for obtaining and cloning cDNA are well known and described by Sambrook et al., supra, and Ausubel et al., supra. Accordingly, cDNA can be cloned by standard procedures and the resulting clones screened with a suitable probe for cDNA coding for the variable regions defined herein. After the desired clones have been isolated, the cDNA may be manipulated in essentially the same manner as genomic DNA.

In addition, the sequences can be obtained by polymerase chain reaction (PCR), after the sequences of the mRNAs have been determined from cDNA by use of primers from the constant regions. From the cDNA sequences of the variable region exons, PCR primers are used to amplify the variable region exons. These PCR primers will have non-homologous extensions which allow insertion into appropriate expression vectors.

Alternatively, the first DNA sequences, containing the requisite genetic information for light and heavy chain variable region specificity for CEA, may be synthetically prepared using conventional procedures.

After confirmation of the MAb DNA sequences in the vector, transfection into eukaryotic host cells, and expression of chimeric antibody, the supernatants are screened for binding to CEA by detection of their human constant regions.

The second DNA sequences of the DNA constructs of the invention, encoding light and heavy chain constant regions of chimeric antibodies, can be cloned from genomic DNA and cDNA, or prepared synthetically. The use of DNA sequences coding human constant regions is expected to result in the production of chimeric light and heavy chain polypeptides which minimize immunogenicity. Preferred for use are the DNA sequences derived from the human light (kappa, and allotypes thereof) chain and the human heavy (gamma or other classes; and the various isotypes or allotypes thereof) chain genes. More preferred are the human gamma isotypes $\gamma 1$ and $\gamma 4$, each of which confers unique biological properties to the resultant chimeric antibodies. For a general review of human gamma isotypes, see, for example, "The Human IgG Subclasses", R. G. Hamilton, Doc. No. CB0051-289, Calbiochem Corporation (1989).

The recombinant DNA techniques necessary to prepare the chimeric DNA constructs of the invention, and incorporate these constructs into appropriate recombinant DNA cloning vectors and DNA expression vectors, are known in the art. See, for example, Sambrook, supra, and Ausubel, supra.

The DNA constructs of the present invention, containing the genes encoding for light and heavy chain chimeric polypeptides, are introduced into appropriate eukaryotic host cells as part of an expression vector. In general, such vectors contain control sequences which are derived from species compatible with a host cello The vector ordinarily carries a specific gene(s) which is (are) capable of providing phenotypic selection in transformed cells. These constructs can be contained on a single eukaryotic expression vector or maintained separately, with separate expression vectors each comprising a single chimeric gene construct. For expression of the chimeric polypeptides it is necessary to include transcriptional and translational regulatory sequences which are functional in the selected eukaryotic host cells.

A wide variety of recombinant host-vector expression systems for eukaryotic cells are known and may be used in the invention. For example, *Saccharomyces cerevisiae*, or common baker's yeast, is the most commonly used among eukaryotic microorganisms, although a number of other strains, such as *Pichia pastoris*, are available. Cell lines derived from multicellular organisms such as Sp2/0 or Chinese Hamster Ovary (CHO), which are available from the ATCC, may also be used as hosts. Typical vector plasmids suitable for eukaryotic cell transformations are, for example, pSV2neo and pSV2gpt (ATCC), pSVL and pSVK3 (Pharmacia), and pBPV-1/pML2d (International Biotechnology, Inc.).

The eukaryotic host cells useful in the present invention are, preferably, hybridoma, myeloma, plasmacytoma or lymphoma cells. However, other eukaryotic host cells may be suitably utilized provided the mammalian host cells are capable of recognizing transcriptional and translational DNA sequences for expression of the chimeric proteins; processing the leader peptide by cleavage of the leader sequence and secretion of the chimeric proteins; and providing post-translational modifications of the chimeric proteins, e.g., glycosylation.

Accordingly, the present invention provides eukaryotic host cells which are transformed by recombinant expression vectors comprising the chimeric gene constructs disclosed herein and which are capable of expressing the chimeric proteins of the invention. The transformed host cells of the invention, therefore, comprise at least one DNA construct comprising the chimeric light and heavy chain genes described herein, and transcriptional and translational sequences which are positioned in relation to the light and heavy chain-encoding DNA sequences to direct expression of these chimeric proteins.

The host cells used in the invention may be transformed in a variety of ways by standard transfection procedures well known in the art. Among the standard transfection procedures which may be used are electroporation techniques, protoplast fusion and calcium-phosphate precipitation techniques. Such techniques are generally described by F. Toneguzzo et al., *Mol. Cell. Biol.*, 6:703–706 (1986); G. Chu et al., *Nucleic Acid Res.*, 15:1311–1325 (1987); D. Rice et al., *Proc. Natl. Acad. Sci. USA*, 79:7862–7865 (1979); and V. Oi et al., *Proc. Natl. Acad. Sci. USA*, 80:825–829 (1983).

The recombinant expression vectors comprising the chimeric constructs of the present invention are transfected sequentially into a host cell. For example, the expression vectors comprising the chimeric light chain DNA constructs are first transfected into the host cells and transformed host cells expressing the chimeric light chain polypeptides are selected by standard procedures known in the art. The expression vectors comprising the chimeric heavy chain DNA constructs are, thereafter, transfected into the selected light chain expressing host cell. Alternatively, both the chimeric light and heavy chain expression vectors can be introduced simultaneously into the host cells.

The novel chimeric antibodies provided by the present invention are useful for both invitro and invivo application. For example, the chimeric antibodies of the invention may be utilized in in vitro immunoassays for the detection of CEA and monitoring of the tumor-associated antigen, e.g., during therapy. Moreover, because it is expected that immunogenicity will be substantially reduced or eliminated, the chimeric antibodies of the inventions are highly desirable for invivo diagnostic and therapeutic application. Accordingly, the chimeric antibodies provided by the invention are of substantial utility for the invivo imaging and treatment of tumors associated with colorectal and breast carcinomas as well as tumors of the gastrointestinal tract, lung, ovary, and pancreas.

The chimeric antibodies of the invention may be used as unmodified antibodies or may be conjugated to suitable diagnostic or therapeutic agents. Examples of diagnostic or therapeutic agents include radionuclides, such as, $^{125}I$, $^{131}I$, $^{123}I$, $^{111}In$, $^{105}Rh$, $^{153}Sm$, $^{67}Cu$, $^{67}Ga$, $^{166}Ho$, $^{177}Lu$, $^{186}Re$, $^{188}Re$, $^{99m}Tc$, $^{90}Y$ and $^{47}Sc$; drugs, such as methotrexate and adriamycin; biological response modifies, such as interferon and lymphokines; and toxins, such as ricin.

A useful method of labeling antibodies with radionuclides is by means of a bifunctional chelating agent. A bifunctional chelating agent is a chemical compound that has a metal chelating moiety, which is capable of sequestering or chelating metals, and a reactive group by which the chelating agent is covalently coupled to a protein. Bifunctional chelators are well known in the art and include, for example, those disclosed in European Patent Application 292689; PCT Application WO 89/12631, published Dec. 18, 1989; U.S. Pat. Nos. 4,678,667; 4,831,175; and 4,882,142.

Additionally, antibody fragments retaining the essential binding function of the chimeric antibodies of the invention, or mixtures including the antibodies, may be utilized depending upon the particular clinical application of the invention.

Moreover, a pharmaceutical composition comprising the novel chimeric antibodies of the present invention in a pharmaceutically acceptable, non-toxic, sterile carrier such as physiological saline, or non-toxic buffer is also possible.

The invention will be further clarified by a consideration of the following examples, which are intended to be purely exemplary of the present invention.

EXAMPLES

Example 1

Replacement of Mouse Constant Regions in COL-1

A. Preparation of COL-1 Heavy and Light Chain Variable Region

1. Isolation of COL-1 Heavy Chain Variable Region a. Sequencing of COL-1 Heavy Chain Variable Region RNA Total RNA from COL-1 cells (murine $IgG_{2a}$,κ) [Muraro et al., supra] was extracted by the guanidinium isothiocyanate/CsCl method of Chirgwin et al., *Biochemistry*, 18:5294–5299 (1979). Poly A+ RNA was purified by passage over an oligo dT-cellulose column. RNA sequencing was performed according to Geliebter, Bethesda Research Laboratories *FOCUS* 9:5–8 (1987).

RNA sequencing was initially conducted using oligonucleotides complementary to all four $J_H$ regions, however, only the $J_H1$ oligonucleotide primed synthesis. The sequence of the $J_H1$ oligonucleotide (SEQ ID NO:7) is as follows:

5'-GAGGAGACGGTGACCGTGGTCCC-3'

The RNA sequence data obtained corresponded to 41 nucleotides of the 5' nontranslated region, the entire leader peptide coding region and the entire variable region. This RNA sequence data was used as positive identification for acquisition of genomic DNA clones coding for the variable region.

b. Genomic Cloning of COL-1 Heavy Chain Variable Region

COL-1 DNA was purified from the COL-1 hybridoma line as described in Sambrook et al., supra. A genomic DNA Southern blot hybridization of COL-1 DNA digested with EcoRI indicated a unique 5.6 kb fragment that hybridized with a murine heavy chain $J_H$-Cμ intron hybridization probe. A genomic DNA library was constructed from restriction enzyme-digested, size-fractionated DNA using the lambda bacteriophage cloning vector, λ-ZAP (Stratagene, La Jolla, Calif.) following the manufacturer's protocols for ligation and bacteriophage packaging. Genomic library screening was performed as described in Sambrook et al. supra, using the same heavy chain $J_H$-Cμ intron hybridization probe as employed in the genomic blot hybridization. This hybridization probe detects the productively rearranged variable region gene sequence in an immunoglobulin gene which is directly linked to the constant region gene sequences. Nine hundred thousand plaques were screened and three positively hybridizing plaques were purified. Plasmid recovery from the λ-ZAP bacteriophage was performed as described by Stratagene. The heavy chain variable region gene from COL-1 was isolated as an approximately 5.6 kilobase pair (kb) EcoRI fragment. All three lambda bacteriophage contained the 5.6 kb EcoRI fragment.

c. Sequence of COL-1 Heavy Chain Variable Region Gene

Plasmid DNA was sequenced using the Sequenase™ DNA sequencing kit obtained from United States Biochemicals (USB) (Cleveland, Ohio) following the manufacturer's protocol. DNA sequence was initially performed using a $J_H1$ oligonucleotide for positive identification through comparison with the sequence obtained by RNA sequencing.

In addition to the $J_H1$ oligonucleotide, the following oligonucleotides were used to completely sequence the COL-1 heavy chain variable region gene (SEQ ID NO:3):

DC 108 (SEQ ID NO:8): 5'-CACTATGACTACAGACACATC-CTC-3'

DC 109 (SEQ ID NO:9): 5'-GAGGATGTGTCTGTAGTCAT-AGTG-3'

DC 110 (SEQ ID NO:10): 5'-CTCTGTGACAGTGGCAATCAC-3'

DC 111 (SEQ ID NO:11): 5'-GTGATTGCCACTGTCACAGAG-3'

The COL-1 heavy chain variable region utilized an SP2.2 D segment [see, Kabat et al., *Sequences of Proteins of Immunological Interest*, Fourth Edition, U.S. Department of Health and Human Services, National Institutes of Health (1991)] in its productive rearrangement. The heavy chain variable region of COL-1 fits the sequence criteria to be classified as a member of mouse heavy chain subgroup II(C) by Kabat et al., supra, and as a member of Group 1 by Dildrop, *Immunol. Today*, 5:85–86 (1984). The predicted amino acid sequence is that of SEQ ID NO:4.

A comparison was made between the mRNA sequence obtained above and the DNA sequence. Based on this comparison, the plasmid clone was identified to contain the correct DNA sequence to code for the COL-1 heavy chain variable region.

The nucleotide sequence of the COL-1 heavy chain variable region was compared to the GenBank (version 62) DNA Sequence database and the precursor germline gene was identified. This gene has been designated $V_H2b-3$ [Schiff et al., *J. Exp. Med.*, 163:573–587 (1986)]. There are no productively rearranged genes in the GenBank® database (version 65) that are derived from $V_H2b-3$. A comparison of the nucleotide sequence of COL-1 heavy chain variable region and the variable region of $V_H2b-3$ shows that there are three somatic mutations that lead to three amino acid substitutions.

2. Isolation of COL-1 Light Chain Variable Region a. Sequencing of COL-1 Light Chain Variable Region mRNA Total RNA from COL-1 cells (murine $IgG_{2a}$,κ) was prepared as described above in I.A.1.a.

Initial sequence data was collected on the light chain variable region of COL-1 using a murine κ specific oligonucleotide designated Cκ. The nucleotide sequence of Cκ (SEQ ID NO:12) is as follows:

5'-GGAAGATGGATACAGTTGGTGC-3'

Further sequence was obtained using an J1 oligonucleotide specific for the murine J1, and an COL1LFR3 oligonucleotide designed from the framework 3 region. The nucleotide sequence for J1(−) (SEQ ID NO:13) and COL1LFR3(−) (SEQ ID NO:14) are as follows:

J1 (−): 5'-CGTTTGATTTCCAGCTTGGTGCC-3'

COL1LFR3(−): 5'-CAGACCCACTGCCACTGAACC-3'

The sequence obtained using the above oligonucleotides as primers corresponded to 19 nucleotides of the 5' non-translated sequence, the entire leader peptide coding region and the entire variable region. This RNA sequence data was used as positive identification for acquisition of DNA clones coding for the variable region.

b. PCR-mediated Cloning of COL-1 Light Chain Variable Region

Using the sequence information obtained from the sequencing of the COL-1 light chain RNA, oligonucleotide primers were designed to be used in a polymerase chain reaction (PCR) amplification [Saiki et al., *Science*, 239:487–491 (1989)] to isolate the COL-1 light chain variable region cDNA. The primers, 5' primer: designated COL1L5PCR and 3' primer: designated COL1L3PCR, were designed to yield a DNA product that could be directly cloned into an expression vector that contained the human κ constant region gene sequences. The sequence of the primers used were:

COL1L5PCR (SEQ ID NO:15)

5'-CTCGGATCCTCATTGTCCATTACTGACTAC
AGGTGCCTACGGTGACATTGTGCTGACACAG-3' BamHI

COL1L3PCR (SEQ ID NO:16)

5'-CATTAAGCTTAGAAAAGTGTACTT
ACGTTTGATTTCCAGCTTGGTGCC-3+ HindIII

The double underlined nucleotides indicate the splice acceptor and donor sites in the introns.

An initial reverse transcriptase cDNA synthesis step was performed prior to the PCR amplification. Briefly, one microgram of COL-1 poly $A^+$ RNA was primed with COL1L3PCR and 13.5 units of AMV reverse transcriptase (Boehringer Mannheim, Indianapolis, Ind.). The subsequent PCR amplification yielded a 397 bp fragment. This fragment was digested with BamHI and HindIII and cloned into the human K constant region gene expression vector pRL1003 (see Example I.B.3. below). Several clones were obtained having the correct restriction enzyme profile.

c. Sequence of COL-1 Light Chain Variable Region

DNA sequencing was performed by directly sequencing plasmid DNA using the Sequenase™ DNA sequencing kit (United States Biochemicals, Cleveland, Ohio) following the manufacturer's protocol.

The DNA sequence was determined for two clones using the primers HindIII Ck (−) and COL1LFR3(−). The sequence (SEQ ID NO:17) of HindIII Ck (−) is as follows:

5'-AGAGGATATTGAAATAATTAAATAGCAC-3'

The sequences of the two clones were identical.

The nucleotide and predicted amino acid sequences of the COL-1 light chain variable region are given by SEQ ID NO:1 and SEQ ID NO:2, respectively. The light chain variable region sequence matched the sequence determined from RNA sequencing and indicated that the clone contained the productively rearranged COL-1 light chain variable region sequences.

The nucleotide sequence of the COL-1 light chain variable region was compared to the GenBank version 62 DNA Sequence database. This comparison revealed that the COL-1 light chain variable region was derived from the germline $V_K$-21E 1.5 Kb gene (Heinrich, *J. Exp. Med.*, 159:417–435 (1984). No other productively rearranged variable region genes derived from $V_K$-21E were found in the database. A comparison between the nucleotide and predicted amino acid sequence of the COL-1 light chain variable region and the VK-21E 1.5 Kb gene indicates there are 5 somatic mutations that lead to 5 amino acid substitutions in the COL-1 light chain variable region. The light chain variable region of COL-1 fits the sequence criteria to be classified as a member of mouse kappa light chain III by Kabat et al. supra.

B. Chimeric COL-1 Gene Constructs

1. Human Constant Region Genes a. Human heavy chain constant region genes

Plasmid constructs containing the γ1 and γ4 human heavy chain constant regions (pγ1, and pγ4) were provided by Dr. Ilan R. Kirsch of the National Cancer Institute, Bethesda, Md. Restriction enzyme mapping was performed on these genes to confirm their identity.

A description of γ1 is set forth in Ellison et al., *Nucl. Acid Res.*, 10:4071–4079 (1982) and Takahashi et al., *Cell*, 29:671–679 (1982.)

A description of γ4 is set forth in Ellison et al., *DNA*, 1:11–18 (1981), Krawinkel and Rabbitts, *EMBO J.*, 1:403–407 (1982), and Takahashi et al., supra.

b. Human Light Chain Constant Region Gene

Plasmid pHumC$_K$, containing the human C$_K$ constant regions gene, was obtained from Dr. John Roder, Mt. Sinai Research Institute, Toronto, Ontario. Canada. A description of C$_K$ is set forth in Hieter et al., *Cell*, 22:197–207 (1980).

2. Chimeric COL-1 Heavy Chains

The plasmid vector used to carry the chimeric heavy chain constructs is designated pSV2gpt, set forth in Mulligan and Berg, *Proc. Natl. Acad., Sci. (USA)*, 78:2072–2076 (1981). pSV2gpt is a pBR322 derived plasmid containing the selectable marker gene guanine phosphoribosyl transferase (gpt), which can be used for selective growth in media containing mycophenolic acid. To prepare pSV2gpt as a recipient for the human Cγ1 and Cγ4 exons, it was digested with EcoRI and BamHI. The digested DNA was fractionated on a 4 percent polyacrylamide gel and the 4.5 kb vector fragment was recovered from the gel by electroelution as described in Sambrook et al., supra. This linearized plasmid is able to accept EcoRI-BamHI ended fragments.

The 5' HindIII site, present on the human γ1 constant region exon fragment, was linker converted to an EcoRI site while the PouI site, located 3' to the γ1 exons, was linker converted to a BamHI site for directed cloning into the EcoRI-BamHI sites of pSV2gpt. For the γ4 constant region exons, instead of linker converting the HindIII site to an EcoRI site and a 3' site to BamHI, the EcoRI and BamHI sites that exist in the pBR322 derived vector sequences were used for directed cloning into the EcoRI-BamHI sites of pSV2gpt. The resulting plasmids were designated pSV2-gpt. γ1-2.3 and pSV2-gpt γ4, respectively.

Figure 2:
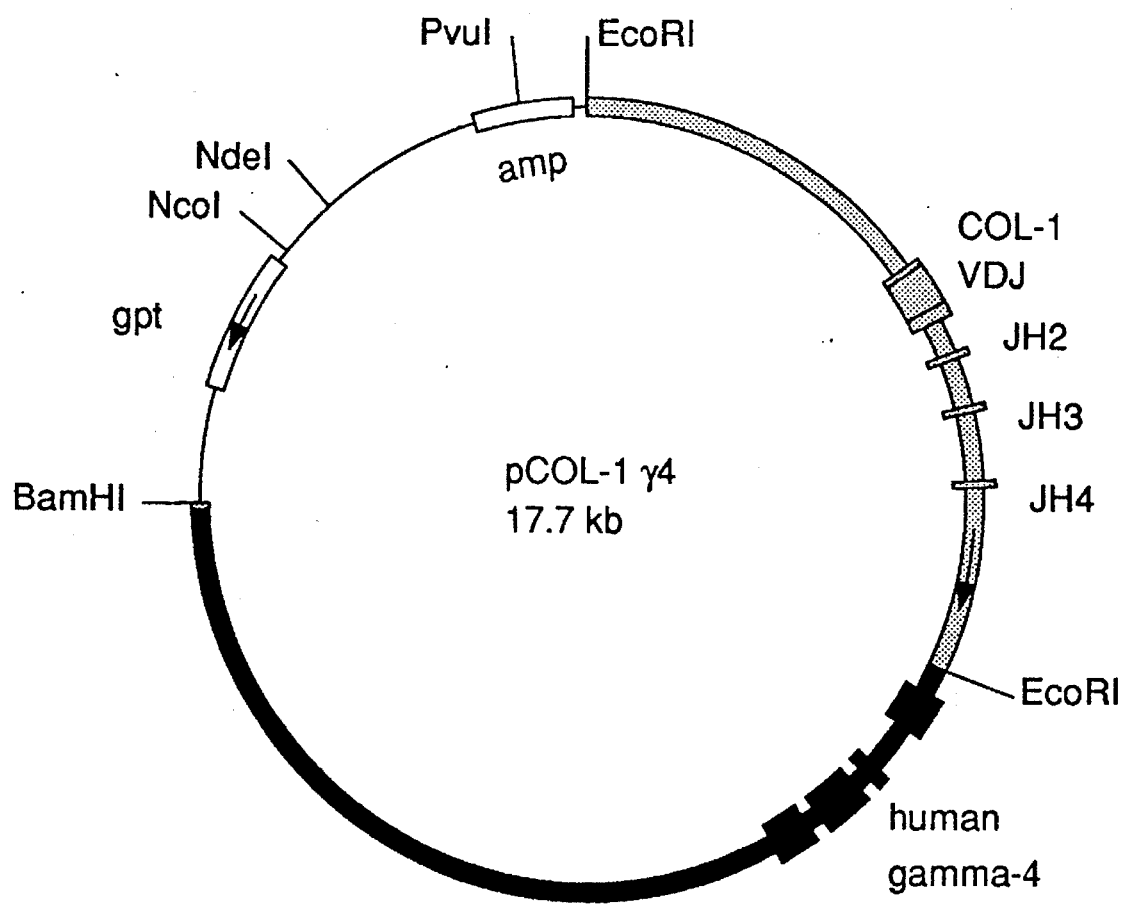
FIG. 2 illustrates the plasmid map of pCOL-1 γ4. The murine COL-1 heavy chain variable region is indicated by the stippled bar and the human γ4 constant region is indicated by the black bar.

The approximately 5.6 kb EcoRI fragment containing the COL-1 heavy chain variable region was ligated into the EcoRI site of the human γ1 and γ4 constant region expression vectors, pSV2-gpt γ1-2.3 and pSV2-gpt γ4, respectively, to generate the chimeric COL-1 heavy chain variable region-human constant region genes contained in plasmids pCOL-1 γ1 (FIG. 1) and pCOL-1 γ4 (FIG. 2), respectively. Prior to electroporation, both of these plasmids were linearized with the restriction endonuclease PvuI at a site that would not interrupt the chimeric gene transcriptional unit. These plasmids are derived from the plasmid pSV2gpt (Mulligan et al., supra) and their presence in transformed mammalian cells can be positively selected for by growth in the presence of mycophenolic acid.

3. Chimeric Light Chain

Figure 3:
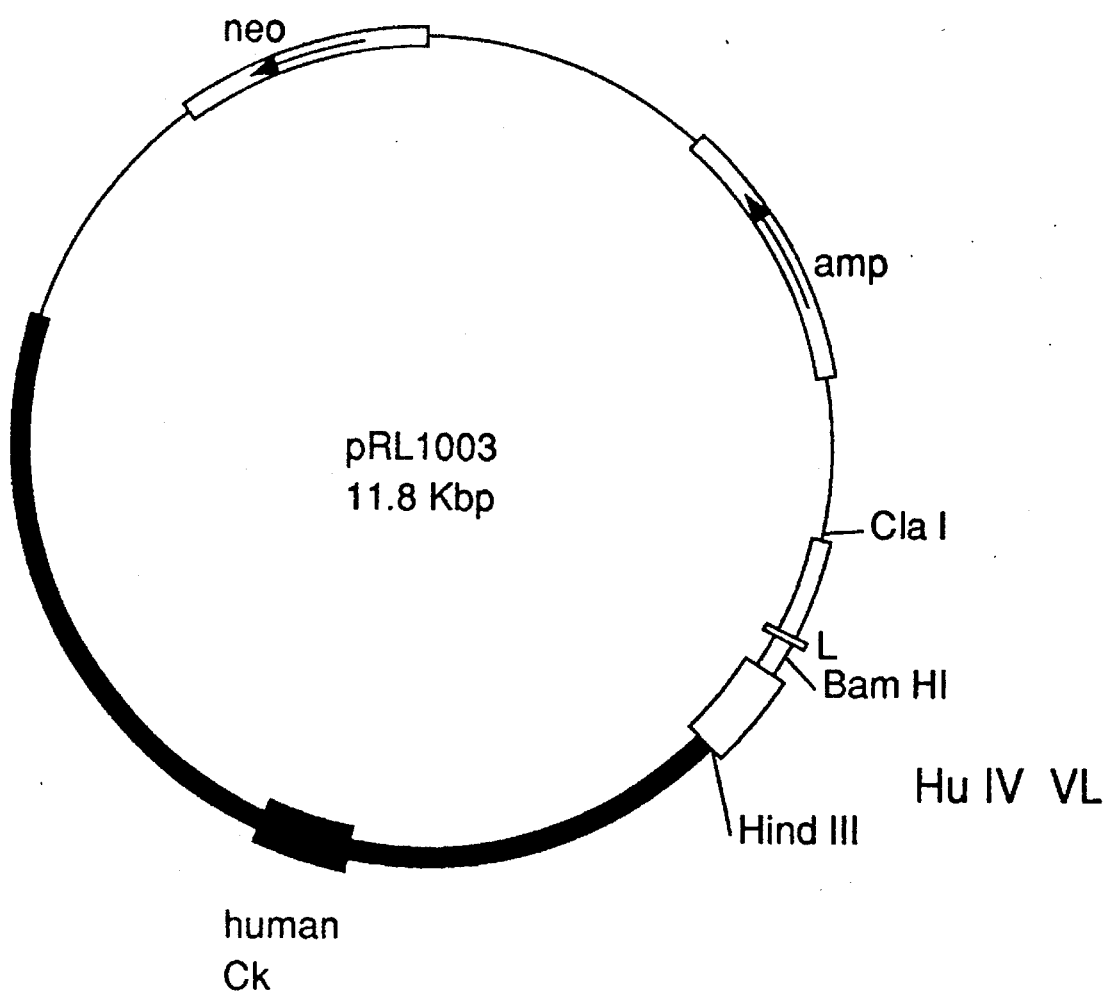
FIG. 3 illustrates the plasmid map of pRL 1003. This is a universal light chain expression vector in that any BamHI-HindIII $V_L$ DNA fragment cloned in the comparable sites of pRL 1003 can give a chimeric light chain polypeptide.
Figure 4:
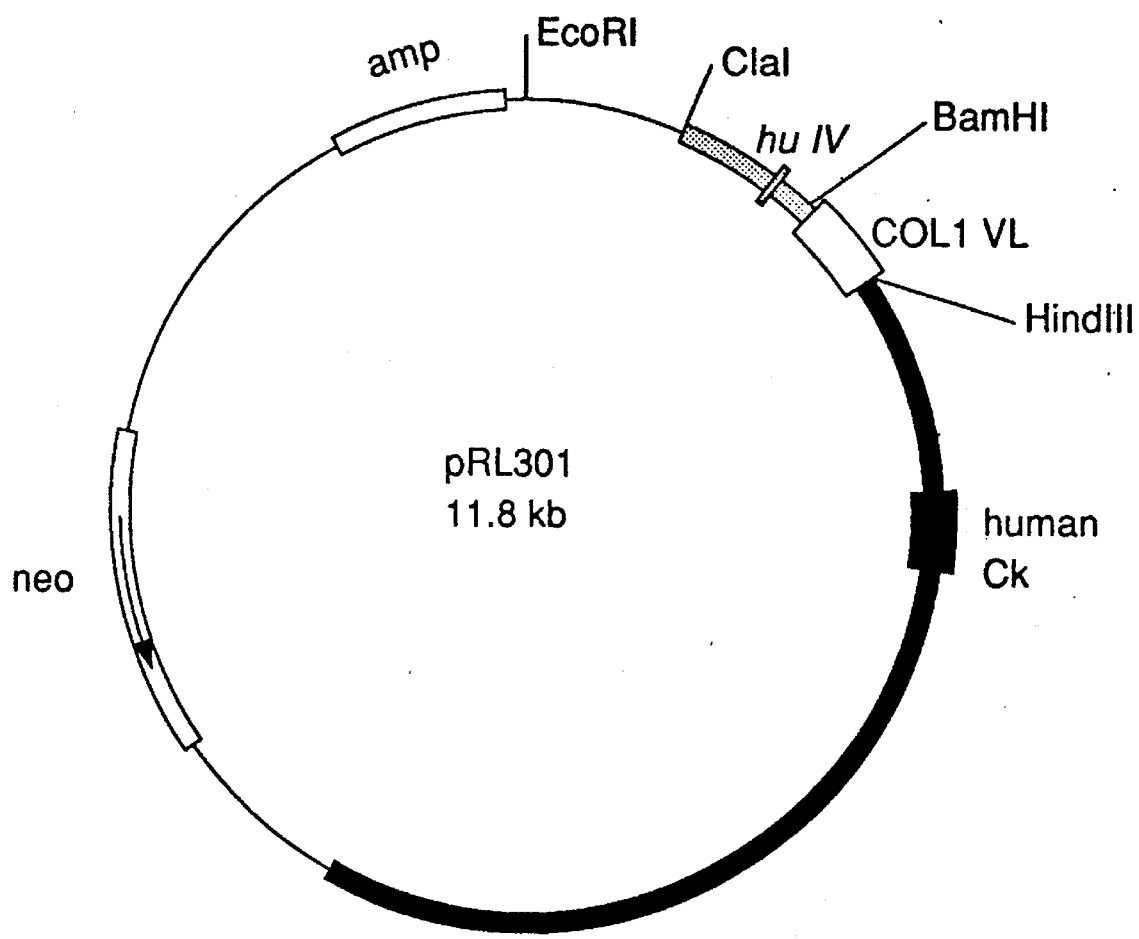
FIG. 4 illustrates the plasmid map of pRL 301. The murine COL-1 light chain variable region is indicated by the open bar, the human κ constant region is indicated by the black bar and the the human Subgroup IV promoter region is indicated by the stippled bar.

The cloning of the COL-1 light chain variable region was accomplished utilizing a "universal" light chain cloning/ expression vector (see A.2.b. above) shown in FIG. 3. This plasmid is designated pRL1003. Not only does this vector allow for rapid cloning of antibody light chain variable regions, but.it results in a transcriptionally intact chimeric light chain gene utilizing a human light chain variable region promoter (derived from Subgroup IV), the human $_K$ intron enhancer and the human $_K$ constant region. The "universal" light chain cloning/expression vector is a derivative of pSV2neo [Southern and Berg, *J. Mol. App. Gen.*, 1:327 341 (1982)] and its existence in transformed mammalian cells can be positively selected for by growth in the presence of an analog of neomycin, G-418, available under the trade name Geneticin from Life Technologies, Grand Island, N.Y. The plasmid containing the chimeric COL-1 light chain was designated pRL301 and is shown in FIG. 4. Prior to electroporation, this plasmid was linearized by digestion with the restriction enzyme ClaI such that the chimeric light chain gene was left intact.

C. Transformation of Chimeric Gene Plasmids into Mouse Myeloma Cells

1. Targeted Transformation

Using a method designated targeted transformation, constructs containing light and heavy chain chimeric immunoglobulin genes were sequentially transformed into Sp2/0 mouse plasmacytoma cells. This method involves transforming cells with a chimeric light chain vector containing a drug-resistance gene, for example neomycin phosphotransferase (neo$^r$), and then selecting for the cells that incorporate that gene by using a medium containing a selectable drug, in this case, Geneticin at a concentration of 1 mg/mL. A second transformation integrates a chimeric heavy chain vector with another drug selection gene, gpt. Selection is then performed using a medium containing both Geneticin and 0.3 µg/mL mycophenolic acid, 250 µg/mL xanthine, and 10 µg/mL hypoxanthine for selection of the neo$^r$ and gpt genes.

2. Preparation of neo Resistant Transformed Sp2/0 Cell Lines Carrying Chimeric COL-1 Light Chain Gene Construct Sp2/0 mouse plasmacytoma cells (ATCC number CRL 1581, Rockville, Md.) were initially transformed with the light chain-containing vector (pRL301) as follows. Cells were grown in RPMI 1640 medium (Life Technologies, Grand Island, N.Y.) with 5 percent fetal calf serum. Cells were washed in phosphate buffered saline (PBS) and suspended to a concentration of 1×10$^7$ viable cells/mL PBS. About 0.8 mL of cells were transferred to an electroporation cuvette (on ice) containing 20 µg of light chain-containing ClaI linearized pRL301. After 15 minutes on ice, electroporation was performed using a Gene Pulser electroporation apparatus with added capacitance extender (BioRad, Richmond, Calif.) at 0.2 kvolts and 960 µF. The time constant (τ) was generally about 26 msec.

After transformation, cells were allowed to recover on ice for 15 minutes to allow relaxation of perturbed membranes. Afterwards, the cells were suspended in 24 mL of RPMI 1640 medium containing 5 percent fetal calf serum and transferred to a 96 or 24 well tissue culture plate. The cells were incubated at 37° C. and 5 percent CO$_2$ atmosphere.

After 48 hours (to allow for the expression of the drug resistance gene), the medium was removed and replaced with medium containing 1 mg/mL Geneticin.

After 10–14 days, the Geneticin-resistant colonies were evaluated for the production of κ light chains by a $_\kappa$ enzyme linked immunosorbent assays (ELISA). The detection of chimeric light chain expression was performed using a goat anti-human $_\kappa$ (GAHK) trap and GAHK probe. Antibodies used for detection in the ELISA were purchased from Southern Biotech Associates (Birmingham, Ala.). The alkaline phosphatase substrate system was obtained from Kirkegaard & Perry Labs (Gaithersburg, Md.). Subclones were identified on the basis of consistently high values on two separate κ ELISAs. Subclone COL-1$_\kappa$D4/F2 was chosen as the target cell line to receive the chimeric heavy chain genes.

3. Preparation of neo and gpt Resistant Transformed Sp2/0 Cell Lines Carrying Chimeric COL-1 Light. and Heavy Chain Gene Construct COL-1kD4/F2 was used as a target for the chimeric heavy chain constructs. The COL-1kD4/F2 cells were separately electroporated with linearized pCOL-1 γ1 and pCOL-1 γ4. The conditions for electroporation were as described above except that after the electroporation, the cells were suspended in 24 mL of RPMI 1640 medium containing 5 percent fetal calf serum and 1 mg/mL Geneticin and transferred to a 96 or 24 well tissue culture plate. The cells were incubated at 37° C. and 5 percent $CO_2$ atmosphere.

After 48 hours (to allow for the expression of the newly incorporated drug resistance gene gpt), the medium was removed and replaced with the same medium containing in addition, 0.3 μg/mL mycophenolic acid, 250 μg/mL xanthine, and 10 μg/mL hypoxanthine.

After 10 to 14 days, the non-mycophenolic acid sensitive colonies were assayed for the production of antibody using IgG ELISAs. The detection of whole chimeric immunoglobulin was performed using a goat anti-human IgG (GAHIgG) trap and a GAHIgG probe. In some cases, the trap antibody was goat anti-human Ig (GAHIg). Subclones were maintained that gave consistently high IgG ELISA results. A cell line designated ChCOL-1 γ1 was identified that expressed the chimeric COL-1 antibody.

D. In Vitro Characterization of Chimeric COL-1

1. Purification of ChCOL-1 γ1 Protein.

The cell line ChCOL-1 γ1 was chosen to produce antibody for purification of research grade protein. A 1 liter spinner flask of RPMI 1640 containing no selectable drugs was inoculated with about $10^8$ cells and grown for 5 days. At the end of the growth period, the spinner flask contained about $2 \times 10^9$ cells at about 6 percent viability. The culture supernatant containing the chimeric antibody was obtained by centrifugation at 8,000×g for 20 minutes. Final clarification was achieved by filtration through a 0.2 μm Gelman (Ann Arbor, Mich.) filter disc. The ChCOL-1 was bound to a Nygene (Yonkers, N.Y.) Protein A cartridge (50 mg IgG capacity) according to the manufacturer's specifications. The antibody was eluted with 0.1M sodium citrate (pH 3.0) and the pH of the collected fractions was immediately raised to neutrality by the addition of 1M Trizma base (Sigma, St. Louis, Mo.) at pH 9.0. Antibody fractions were pooled and concentrated to about 200 μL using a Centriprep 30 microconcentrator device (Amicon, Danvers, Mass.). Final purification was achieved using a Pharmacia Superose 12 HR16/50 gel filtration column (Piscataway, N.J.) with 0.2M phosphate (pH 7.0) as the column buffer. Approximately 6.8 mg of purified protein were obtained.

2. Sodium Dodecyl Sulfate-Polyacrylamide Gel Electrophoresis (SDS-PAGE) and Isoelectric Focusing (IEF) Gel Analysis of ChCOL-1 γ1

Protein samples of ChCOL-1 γ1 (7.5 μg) were analyzed by denaturing polyacrylaminde gel electrophoresis by the method of Laemmli, *Nature*, 277:630–685(1970). Gradient gels (3–12 percent polyacrylamide) were purchased from Integrated Separation Systems (Hyde Park, Mass.). The gel was stained with Coomassie Brilliant Blue R-250 (Biorad Laboratories, Richmond, Calif.).

An SDS-PAGE analysis of purified ChCOL-1 γ1 under non-reducing conditions yielded a product of about 150,000 daltons. Under reducing conditions, the ChCOL-1 yielded a band of about 50,000 daltons corresponding to the heavy chain and a band of about 25,000 daltons corresponding to the light chain. These results compared favorably with the size expected for chimeric light and heavy chain (γ1) polypeptides. The SDS-PAGE analysis indicated that an intact antibody molecule with heavy and light chains was being expressed by the transformed Sp2/0 cell line ChCOL-1 γ1.

For isoelectric focusing, protein samples (between 15 and 20 μg) were desalted using a Centricon-30 (Amicon, Danvers, Mass.) with three changes of 1 percent glycine buffer. The desalted protein samples were applied to an FMC Bioproducts (Rockland, Me.) agarose IEF gel having a pH gradient of 3 to 10. Isoelectric focusing was performed at a constant power of one watt for the first 10 minutes and then continued at 10 watts for another 90 minutes. The gel was stained with Coomassie Brilliant Blue R-250 and then analyzed using a Biomed Instruments (Fullerton, Calif.) scanning densitometer to determine the isoelectric points. The protein standards were obtained from Biorad Laboratories (Richmond, Calif.) and Sigma (St. Louis, Mo.).

The IEF gel analysis of ChCOL-1 γ1 showed a unique pattern of bands compared to the murine COL-1MAb. Densitometric scanning of the Coomassie blue stained gel indicated that the major band from the ChCOL-1 γ1 sample represented about 81 percent of the total while the fainter, minor band immediately above it represented about 18 percent of the total. Based on the assignment of known pI values to the protein standards, the 2 major ChCOL-1 γ1 isoelectric forms were calculated to be 7.8 and 7.6. The minor form at pI=7.6 is likely the result of a post-translational deamidation of a glutamine or asparagine residue which can occur in proteins produced from mammalian cells [Wilson et al., *J. Biol. Chem.*, 257:14830–14834 (1982)].

3. ChCOL-1 γ1 $NH_2$ Terminal Protein Sequence

Eighty micrograms of ChCOL-1γ1 were reduced, alkylated and the heavy and light chains separated by reverse phase high performance liquid chromatography. The separated heavy and light chains were subjected to amino terminal amino acid sequence analysis using the Edman degradation method as modified by G. Tarr (1986) in "Manual Edman Sequencing System", *Microcharacterization of Polypeptides: A Practical Manual*, (John E. Shively, ed., Humana Press, Inc., Clifton, N.J., pp 155–194.

Ten amino acid residues were determined from both the light chain and heavy chain. The sequences matched the DNA encoded predicted sequence for the mature protein, demonstrating that the chimeric protein is processed correctly in both chains.

4. CEA and LS174T ELISAs

The ability of ChCOL-1 γ1 to bind to CEA was tested in two different ELISA procedures. The first ELISA was a CEA ELISA. In this case, purified CEA (Chemicon, El Segundo, Calif.) was used as the trap and GAHIgG was used as the probe. In addition, the ChCOL-1 γ1 antibody was also tested for binding to LS174T cells. LS174T cells (ATCC number CL 188) are derived from a human colon carcinoma cell line that express CEA and other tumor antigens [Muraro et al., *Cancer Res.*, 45:5769–5780 (1985); Muraro et al., *Cancer Res.*, 48:4588–4596 (1988)]. Both ELISAs demonstrated that ChCOL-1 γ1 bound to CEA and LS174T cells respectively and was recognized by anti-human immunoglobulin reagents.

E. In Vivo Characterization of Chimeric COL-1 Antibody

The chimeric antibody used in the animal studies shown in Tables I and II below was labeled with $Na^{125}I$ using as an iodination reagent 1,3,4,6-tetrachloro-3α-6α-diphenylglycoluril (IODO-GEN™ Pierce Chemical, Rockford, Ill.) More specifically, from about 0.5–2 mg of chimeric antibody was adjusted to about 0.5 mL 0.1M sodium phosphate buffer (pH 7.2) and then added to a 12 cm×75 cm glass tube coated with 50 μg of IODO-GEN™ followed by addition of from 0.1–0.5 mCi of $Na^{125}I$ (New England Nuclear, Boston, Mass.). After a 2 min. incubation at room temperature, the protein was removed from the insoluble IODO-GEN™, and the unincorporated $^{125}I$ was separated from the antibody by gel filtration through a 10 mL column of Sephadex G-25 using PBS as the buffer. The iodination protocol yielded radiolabeled IgG chimeric antibody with a specific activity of 0.05 to 0.2 μCi/μg.

Female athymic mice (nu/nu) on a CD1 background were obtained from Charles River at approximately 4 weeks of age. Nine days later, the mice were inoculated subcutaneously (0.1 mL/mouse) with the LS174T cells ($1×10^6$ cells/animal).

Athymic mice bearing carcinomas 70 to 400 mg in weight, approximately 12 to 13 days after inoculation of the LS174T cells, were given injections intravenously of from 0.5 to 2.0 μCi (10–50 μg protein) in PBS of the chimeric antibody, which had been iodinated as described above. Groups of five mice were sacrificed at varying times by exsanguination. The carcinoma and normal tissues were excised and weighed, and the counts per minute (cpm) was measured in a gamma counter. The cpm/mg of each tissue was then determined and compared to that found in the carcinoma.

The biodistribution results for ChCOL-1 γ1 are shown in Tables I and II.

TABLE I

Percent Injected Dose per Gram of $^{125}I$-LABELED ChCOL-γ1 Antibody

| Tissue | 5 hours | 24 hours | 48 Hours | 120 Hours |
|---|---|---|---|---|
| Blood, total | 26.73 | 17.04 | 15.33 | 10.67 |
| Liver | 5.5 | 3.40 | 2.44 | 2.14 |

TABLE I-continued

Percent Injected Dose per Gram of $^{125}I$-LABELED ChCOL-γ1 Antibody

| Tissue | 5 hours | 24 hours | 48 Hours | 120 Hours |
|---|---|---|---|---|
| Spleen | 4.81 | 4.20 | 2.67 | 2.42 |
| Kidney | 3.75 | 2.03 | 2.42 | 1.17 |
| Tumor | 11.86 | 25.88 | 26.17 | 26.44 |
| Lung | 18.38 | 5.98 | 4.41 | 3.12 |
| Tumor weight (gram) | 0.30 | 0.23 | 0.13 | 0.17 |

As shown in Table I, at approximately 120 hours post-injection, the injected dose per gram to tumor for ChCOL-1 γ1 was 26.44 percent. ChCOL-1 γ1 was efficient in targeting the human tumor in situ. This demonstrates that the chimeric antibody of the present invention was efficient for in vivo carcinoma targeting.

TABLE II

Percent Injected Dose per Organ of $^{125}I$-LABELED ChCOL-γ1 Antibody

| Tissue | 5 hours | 24 hours | 48 Hours | 120 Hours |
|---|---|---|---|---|
| Blood, total | 38.42 | 23.14 | 20.45 | 16.60 |
| Liver | 6.47 | 3.76 | 3.13 | 2.71 |
| Spleen | 0.57 | 0.33 | 0.26 | 0.23 |
| Kidney | 0.90 | 0.46 | 0.55 | 0.31 |
| Tumor | 3.85 | 5.99 | 3.49 | 4.54 |
| Lung | 3.57 | 0.83 | 0.61 | 0.49 |
| GI Tract | 8.22 | 3.96 | 3.85 | 2.53 |
| Carcass | 54.27 | 40.72 | 41.82 | 33.93 |
| Whole Body Retention | 99.36 | 67.33 | 65.02 | 53.55 |

As shown in Table II, at 120 hours post-injection, the injected dose per organ of tumor for ChCOL-1 γ1 was 4.54 percent. The chimeric monoclonal antibody was efficient in targeting the human tumor in situ. This demonstrates that the chimeric monoclonal antibody of the present invention was efficient for invivo carcinoma targeting and, thus, is useful for in vivo treatment of cancer.

F. Deposit of Cell Lines Producing Chimeric Antibodies

Two cell lines secreting chimeric antibodies, both having a kappa light chain, made by the above example were deposited at the American Type Culture Collection on Dec. 9, 1992. Specifically, the following cell lines have been deposited:

(1) ChCOL-1 γ1: a cell line having COL-1 $V_H$, COL-1 $V_L$, and constant region of human IgG1 (ATCC No. CRL 11217); and (2) ChCOL-1 γ4: a cell line having COL-1 $V_H$, COL-1 $V_L$, and constant region of human IgG4 (ATCC No. CRL 11214).

The present invention is not to be limited in scope by the cell lines deposited since the deposited embodiment is intended as a single illustration of one aspect of the invention and all cell lines which are functionally equivalent are within the scope of the invention.

Example 2

Genetically Altered Versions of Chimeric COL-1

A. Shortened Heavy Chain Gene Constructs

The shortened heavy chain gene constructs, Fab and F(ab')$_2$, for chimeric COL-1 were genetically produced by sequential removal of the C-terminal domains of the γ1 or γ3 human heavy chains. The F(ab')$_2$-like construction was generated by removing both the Cγ2 and Cγ3 domains of the human γ1 heavy chain leaving the hinge and Cγ1 domains. The γ1 isotype was used for construction of the F(ab')$_2$ molecules. However, when designing the Fab-sized molecule, which is ⅓ the size of the intact antibody, removal of the hinge domain would eliminate the site of attachment of the light chain. Therefore, the human γ3 heavy chain was used for the Fab construction. The Cγ1 domain of the human γ3 heavy chain differs from the Cγ1 domain of the human γ1 heavy chain in only 4 out of 98 amino acids. Ser-127 of γ1 Cγ1 is replaced by Cys-127 in γ3 which serves as the site of attachment of the light chain. Of the three other amino acid differences between γ1 and γ3, two of them are conservative replacements (Lys to Arg), Huck et al., *Nucl. AcidsRes.*, 14:1779–1789 (1986).

1. PCR and SOE Methods

PCR was done according to the method described by Saiki, et al., *Science*, 239:487–491 (1988) and splicing by overlap extension (SOE) according to the method described by Hoet al., *Gene*, 77:51–59 (1989) and Horton et al., *Gene*, 77:61–68 (1989).

Template and primer concentrations were 0.1–1.0 ng/mL and 1 nmole/mL, respectively, in 0.1 mL [Saiki et al., supra]. PCR and SOE conditions were: denaturation: 2 minutes at 92° to 96° C.; annealing: 3 minutes at 50° C.; and extension: 10 minutes at 71° to 74° C. (30 cycles).

2. Design of Oligonucleotide Primers for PCR/SOE

The VDJ exon, the Cγ1 exon of γ3, and the hinge and Cγ2 exons of γ1 all posses at their 3' ends the first nucleotide of the first codon of the next exon. This partial codon was omitted when designing the oligonucleotide primers. The primers used in generating the shortened heavy chain gene constructs are as follows:

complementary to the 5' 18 nucleotides of primer a. The 3' half of primer b1 is complementary to the 6 complete C-terminal codons of the Cγ1 exon of human γ3. The 3' half of primer b2 is complementary to the 6 complete C-terminal-codons of the hinge exon of human γ1.

3- Preparation of neo and gpt Resistant Transformed Sp2/0 Cell Lines Carrying Chimeric COL-1 Light and Shortened Heavy Chain Gene Constructs (Fab and F(ab')$_2$)

Figure 5:
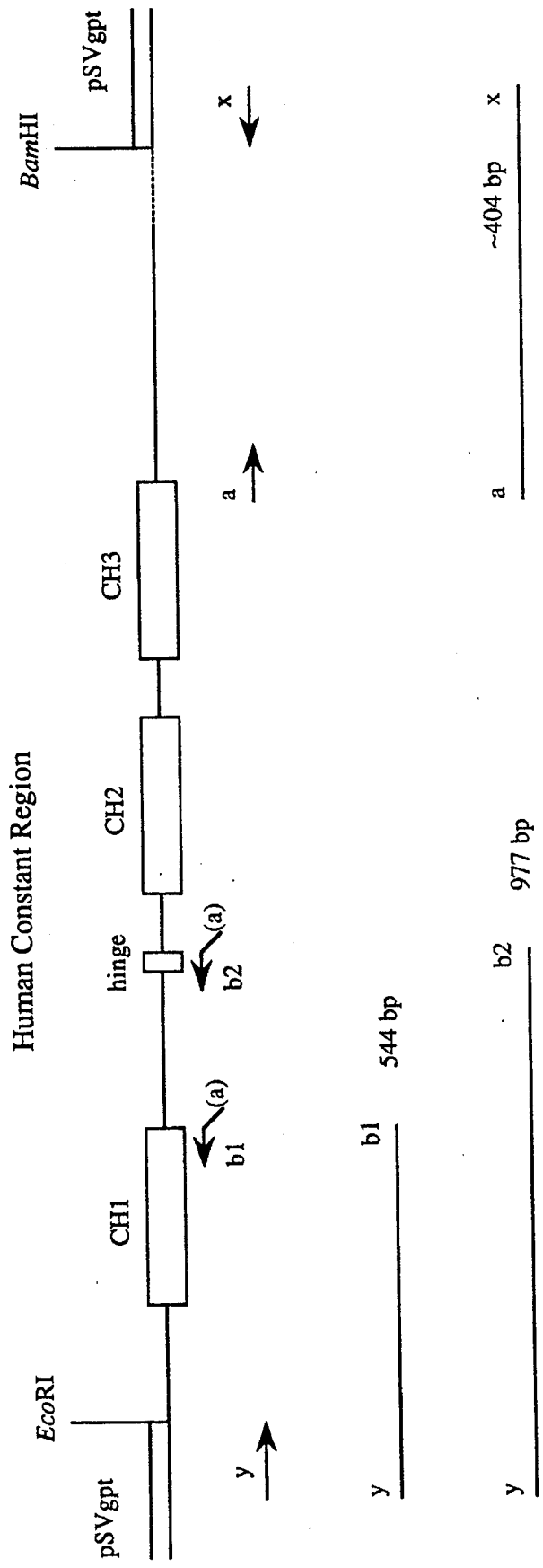
FIG. 5 illustrates the human heavy chain constant region and the oligonucleotide primers (with wagging tails), used to generate the DNA fragments a-x, y-b1 and y-b2.

The general procedure utilizing SOE to construct the shortened heavy chains of the present invention is illustrated in FIG. 5. The fragment a-x (~404 basepairs (bp)) was generated by PCR using the oligonucleotide primers, a and x, and the NdeI-linearized template, pγ1-gpt, which contains the human γ1 gene. Fragment y-b1 (544 bp) was produced by PCR using the primers y and b1 on the pSV2gptγ3 template, a plasmid construct similar to pSV2gptγ1 and pSV2gptγ4 which has the human γ3 gene in place of the human γ1 or γ4 gene. Fragment y-b2 (977 bp) was produced on the pSV2gptγ1-2.3 template using the primers y and b2. The fragments y-b1-x (~948 bp) and y-b2-x (~1381 bp) were generated by SOE technology after annealing the fragments y-b1 and y-b2, respectively with fragment a-x followed by PCR extension with primers y and x.

After purification, the two DNA fragments are mixed, denatured, and re-annealed over the regions of overlap derived from the non-annealing segment. After another PCR, using the outermost oligonucleotide primers (a and d), the overlapping fragments are extended and amplified as a single fragment.

Genes for the heavy chain constant regions all encode lysine as the last amino acid after glycine and before the termination codon [Dunnick et al., *Nucl. Acids Res.*, 8:1475–1484 (1980); Kabat et al., *Sequences of Proteins of Immunological Interest*, U.S. Department of health and Human Services, National Institutes of Health, 5th. edition y (SEQ ID NO:18)
    5'-GGCCCTTTCGTCTTCAAGAATTC-3'
                                     EcoRI x (SEQ ID NO:19)
    5'-TATCTTATCATGTCTGGATCC-3'
                                  BamHI a (SEQ ID NO:20)
    5'-GGTAAATGAGTGCGACGG-3' b1 (SEQ ID NO:21)
    5'-CCGTCGCACTCATTTACCAACTCTCTTGTCCACCTT-3' b2 (SEQ ID NO:22)
    5'-CCGTCGCACTCATTTACCTGGGCACGGTGGGCATGT-3'

The sequence of primer y was derived from the DNA sequence 5' of the EcoRI site of the pSV2gpt [Mulligan et al, *Proc. Natl. Acad. Sci. USA*, 78:2072–2076 (198 1)]. The sequence of primer x was derived from the DNA sequence 3' of the BarnHi site of pSV2gpt (Mulligan et al., supra). The region from which these sequences were derived was originally cloned from pBR322. The sequence of primer a begins with the last two codons (Gly-Lys) of the Cγ3 exon of Human γ1.

The sequences of primers b1, and b2 were designed so that the 5' half would be non-annealing and be exactly (1991)]. However, the C-terminus of secreted mature heavy chain protein has been found to be glycine, (Kabat et al., supra), indicating post-translational processing of the terminal lysine. Because of the possibility that this post-translational processing may be required for efficient expression, each shortened construct was terminated with the last two amino acids of the Cγ3 domain of the human γ1 heavy chain. Thus, the 404 bp DNA fragment a-x, starts with the Gly-Lys and termination codons, and includes the polyadenylation signal sequence. This fragment was used as the 3' joining fragment for all of the constructs. Since the DNA sequence of the 3'-most 190 bp of this fragment is not known, the PCR was performed from a 3' primer derived from the adjacent vector sequence which is known and included the BamHI restriction site of the fragment.

The initial products of the first two PCR's, fragments y-b1 and a-x were purified and subjected to SOE reaction which generated the y-b1-x fragment for the Fab vector construction. The genetic F(ab')$_2$ fragment was constructed by similar methods utilizing the 3'primer b2 and the human γ1 template, which yielded the y-b2-x fragment after SOE reactions. After phenol/chloroform extraction and ethanol precipitation of the SOE reactions, the fragments were digested with both EcoRI and BamHI and gel purified. Each fragment was ligated with the EcoRI/BamHI fragment of the pSV2-gpt vector.

The EcoRI fragment containing the COL-1 heavy chain variable region was ligated into the EcoRI site of each of the shortened heavy chain vectors in the correct orientation as described in Example 1.

4. Selection and Expression

Each of the chimeric COL-1 shortened heavy chain vectors was linearized with PvuI and electroporated into target cells (COL-1κD4/F2) which express the chimeric COL-1 light chain. Mycophenolic acid-resistant colonies were selected for expression of shortened heavy chain ChCOL-1 antibodies by ELISA for binding to plates coated with CEA (AMAC, Inc., Westbrook, Me.) and detected with alkaline phosphatase-conjugated goat anti-human kappa antibody (Southern Biotechnology Associates, Inc., Birmingham, Ala.).

B. In vivo Characterization of Chimeric COL-1 Fab and F(ab')$_2$

After purification from culture supernatants, the ChCOL-1 Fab was used in animal studies by radiolabeling with Na$^{125}$I and detecting its biodistribution as described in Example 1.

The biodistribution results for ChCOL-1 Fab are shown in Tables III and IV.

TABLE III

Percent Injected Dose per Gram of $^{125}$I-LABELED ChCOL-Fab γ1 Antibody

| Tissue | 15 min. | 30 min. | 2 Hours | 5 Hours | 24 Hours |
|---|---|---|---|---|---|
| Blood, total | 19.13 | 10.61 | 5.21 | 2.71 | 0.32 |
| Liver | 4.40 | 3.06 | 1.81 | 1.07 | 0.35 |
| Spleen | 4.29 | 3.49 | 2.33 | 1.42 | 0.36 |
| Kidney | 117.42 | 96.50 | 17.04 | 7.91 | 1.36 |
| Tumor | 2.45 | 3.28 | 3.43 | 2.19 | 0.98 |
| Lung | 6.51 | 14.67 | 3.85 | 2.39 | 0.51 |
| Tumor weight (gram) | 0.23 | 0.19 | 0.33 | 0.24 | 0.17 |

As shown in Table III, at approximately 24 hours post-injection, the injected dose per gram to tumor for ChCOL-1 Fab was 0.98 percent. ChCOL-1 Fab was efficient in targeting the human tumor insitu. The results demonstrate that the chimeric antibody fragments of the present invention are efficient for in vivo carcinoma targeting.

TABLE IV

Percent Injected Dose per Organ of $^{125}$I-LABELED ChCOL-γ1 Fab Antibody

| Tissue | 15 min. | 30 min. | 2 Hours | 5 Hours | 24 Hours |
|---|---|---|---|---|---|
| Blood, total | 30.11 | 16.36 | 78.3 | 3.89 | 0.52 |
| Liver | 6.41 | 3.94 | 2.28 | 1.26 | 0.49 |
| Spleen | 0.60 | 0.42 | 0.28 | 0.18 | 0.05 |
| Kidney | 34.89 | 24.52 | 5.53 | 1.95 | 0.39 |
| Tumor | 0.59 | 0.58 | 1.14 | 0.54 | 0.17 |
| Lung | 1.27 | 2.15 | 0.2 | 0.36 | 0.09 |
| GI Tract | 6.09 | 9.60 | 20.85 | 11.69 | 0.29 |
| Carcass | 36.91 | 33.72 | 30.01 | 16.30 | 1.46 |
| Whole Body Retention | 97.45 | 85.27 | 65.32 | 33.14 | 3.26 |

As shown in Table IV, at 24 hours post-injection, the injected dose per organ to tumor for ChCOL 2D1 Fab was 0.17 percent. The chimeric antibody fragment was efficient in targeting the human tumor insitu. These results demonstrate that the chimberic antibody fragments of the present invention are efficient for in vivo carcinoma targeting.

C. Mutant Chimeric COL-1 (ChCOL-1 R') 1. Genetic Mutation in JH

The oligo, designated COL1x-R'(3'), was designed based on mRNA sequence data from the COL-1 heavy chain. The nucleotide sequence of this oligo was based on the assumption that there were no differences from the germline J$_H$1 sequence. The nucleotide sequence of COL1x-R'(3') (SEQ ID NO:23) is as follows:

5'-GATGCGGCCGCTCTTACC [T]GA GGA GAC GG[T] GAC C-3'
　　　　　NotI

The bracketed nucleotides indicate the differences of the cloned COL-1 V$_H$ genomic DNA sequence from the germline J$_H$1 sequence. The first T difference is a silent mutation, while the second T difference results in a mutation of Ala$^{110}$ to Thr$^{110}$. The double underlined nucleotides indicate the splice donor site in the intron.

a. PCR amplification of COL1x-R' Heavy Chain from mRNA

The reverse transcription reaction utilized (in 90 μL) 1 μg of COL-1 poly A+ mRNA; 10 pmoles of COL1x-R'(3'); and 9 μL of 10× buffer (1×=50 mM Tris (pH=8.2); 6 mMMgCl$_2$; 100 mM NaCl); 0.22 mM dNTPs. The sample was heated to 80° C. for 3 minutes then cooled to 45° C. Then 0.5 μL (12.5 units) of AMV reverse transcriptase (Boehringer Mannheim, Indianapolis, Ind.) was added and allowed to extend for 30 minutes. The PCR was continued by the addition of 1 μL 10× buffer; 100 pmoles of COL1-y; 90 pmoles of COL1x-R'; 0.5 μL (2.5 units) of Taq polymerase (Stratagene, La Jolla, Calif.) The nucleotide sequence of COL1-y (SEQ ID NO:24) is as follows:

5'-CGT<u>GTCGAC</u>AGGC ATC AAT TCA GAG G-3'
   SalI

The double underlined nucleotides indicate the splice acceptor site in the intron. After covering with 2 drops of mineral oil, thermal cycling between 94° C. 37° C. and 72° C. (30 seconds each) was performed 25 times using a 100 μL reaction volume. The 405 bp PCR product was gel purified. After trimming the ends of this DNA insert with SalI and NotI restriction enzymes, the fragment was ligated into the phosphatased, gel-purified pV-γ1 vector previously digested with SalI and NotI.

2. Preparation of Neo and Gpt Resistant Transformed Sp2/0 Cell Lines Carrying Chimeric COL-1LiMht and Mutant (R') Heavy Chain Gene Constructs The chimeric pCOL1-R' heavy chain vector was electroporated into the cell line expressing the ChCOL-1 light chain, COL-1$_K$D4/F2, after linearization with PvuI.

Drug resistant colonies in 96 well plates were screened by ELISA using both CEA antigen traps and goat anti-human kappa or goat anti-human IgG antibody traps (Southern Biotechnology Associates, Birmingham, Ala.). Chimeric antibody bound to these traps was detected with goat anti-human kappa antibody conjugated with alkaline phosphatase in a standard ELISA assay. Individual primary clones which were positive on all 3 traps were subcloned and the cell lines expressing the highest levels of antibody were each frozen in cryovials. ChCOL-1R' antibodies were purified from culture supernatants as described in Example I using protein A chromatography.

D. In Vivo Characterization of ChCOL-1R'

The ChCOL-1R' for use in animal studies was labeled with Na$^{125}$I and used for detecting carcinoma tissue as described in Example 1. The biodistribution results for ChCOL-1 R' are shown in Tables V and VI.

As shown in Table V, at approximately 120 hours post-injection, the injected dose per gram to tumor for

TABLE V

Percent Injected Dose per Gram of $^{125}$I-LABELED ChCOL-1 R' Antibody

| Tissue | 5 hours | 24 hours | 48 Hours | 120 Hours |
|---|---|---|---|---|
| Blood, total | 22.16 | 13.64 | 11.44 | 10.73 |
| Liver | 5.95 | 2.79 | 2.26 | 2.42 |
| Spleen | 5.18 | 2.41 | 2.17 | 2.24 |
| Kidney | 3.25 | 1.38 | 1.57 | 1.21 |
| Tumor | 8.15 | 23.74 | 31.93 | 42.34 |
| Lung | 6.09 | 3.52 | 3.33 | 3.24 |

TABLE V-continued

Percent Injected Dose per Gram of $^{125}$I-LABELED ChCOL-1 R' Antibody

| Tissue | 5 hours | 24 hours | 48 Hours | 120 Hours |
|---|---|---|---|---|
| Tumor weight (gram) | 0.26 | 0.32 | 0.14 | 0.10 |

ChCOL-1R' was 42.34 percent. ChCOL-1R' was efficient in targeting the human tumor insitu, demonstrating that the ChCOL-1R' of the present invention was efficient for invivo carcinoma targeting.

TABLE VI

Percent Injected Dose per Organ of $^{125}$I-LABELED ChCOL-1 R' Antibody

| Tissue | 5 hours | 24 hours | 48 Hours | 120 Hours |
|---|---|---|---|---|
| Blood, total | 32.32 | 19.30 | 15.91 | 15.79 |
| Liver | 5.95 | 3.45 | 2.87 | 2.85 |
| Spleen | 0.59 | 0.28 | 0.26 | 0.26 |
| Kidney | 0.76 | 0.35 | 0.36 | 0.29 |
| Tumor | 2.04 | 7.33 | 4.44 | 5.63 |
| Lung | 0.89 | 0.57 | 0.51 | 0.47 |
| GI Tract | 7.61 | 3.43 | 3.15 | 2.79 |
| Carcass | 46.10 | 36.60 | 33.16 | 32.00 |
| Whole Body Retention | 82.50 | 62.10 | 55.68 | 51.45 |

As shown in Table VI, at 120 hours post-injection, the injected dose per organ to tumor for ChCOL-1R' was 5.63 percent. Compared with ChCOL-1, the ChCOL-1R' showed approximately 50 percent more accumulation in the tumors at 120 hours post injection.

E. Deposit of Cell Lines Producing Genetically Altered Chimeric Antibodies

Three cell lines secreting genetically altered chimeric antibodies, all having a kappa light chain, made by the above example were deposited at the American Type Culture Collection on Dec. 8, 1992. Specifically, the following cell lines have been deposited: (1) ChCOL 2D1 Fab: a cell line having COL-1 V$_H$, COL-1 V$_L$, and constant region of human IgG3 Fab (ATCC No. CRL 11218); (2) ChCOL 2D1 F(ab')$_2$: a cell line having COL-1 V$_H$, COL-1 V$_L$, and constant region of human IgG1 F(ab')$_2$ (ATCC No. CRL 11216); and (2) ChCOL-1 R': a cell line having COL-1 V$_H$ containing a single amino acid mutation, COL-1 V$_L$, and constant region of human IgG1 (ATCC No. CRL 11215).

The present invention is not to be limited in scope by the cell lines deposited since the deposited embodiment is intended as a single illustration of one aspect of the invention and all cell lines which are functionally equivalent are within the scope of the invention.

While this invention has been described in detail and with reference to specific embodiments thereof, it will be apparent to one skilled in the art that various changes and modifications could be made therein without departing from the spirit and scope of the appended claims.

What is claimed is:

1. A chimeric monoclonal antibody which binds to carcinoembryonic antigen having a light chain variable region with an amino acid sequence the same as that of SEQ ID NO:2.

2. A chimeric monoclonal antibody which binds to carcinoembryonic antigen having a heavy chain variable region with an amino acid sequence the same as that of SEQ ID NO:4 or SEQ ID NO:6.

3. The chimeric monoclonal antibody of claim 2 having an amino acid sequence the same as that of SEQ ID NO:4.

4. The chimeric monoclonal antibody of claim 2 having the amino acid sequence of SEQ ID NO:6.

5. A chimeric monoclonal antibody which binds to carcinoembryonic antigen having a light chain variable region the same as that of SEQ ID NO:2 and a heavy chain variable region having the amino acid sequence the same as that of SEQ ID NO:4 or SEQ ID NO:6.

6. The chimeric monoclonal antibody of claim 5 wherein the light chain variable region is SEQ ID NO:2 and the heavy chain variable region is SEQ ID NO:4.

7. The chimeric monoclonal antibody of claim 6 wherein the antibody is produced by a cell line selected from consisting of ATCC No. CRL 11214, ATCC No. CRL 11216, ATCC No. CRL 11217 and ATCC No. CRL 11218.

8. The chimeric monoclonal antibody of claim 5 wherein the light chain variable region is the same as that of SEQ ID NO:2 and the heavy chain variable region is SEQ ID NO:6.

9. The chimeric monoclonal antibody of claim 8 wherein the antibody is produced by the cell line ATCC No. CRL 11215.

10. A composition comprising a chimeric monoclonal antibody of claim 5 in a pharmaceutically acceptable, non-toxic, sterile carrier.

* * * * *